US010675298B2

(12) United States Patent
Lanphere et al.

(10) Patent No.: US 10,675,298 B2
(45) Date of Patent: Jun. 9, 2020

(54) PARTICLES

(71) Applicant: Boston Scientific Scimed Inc., Maple Grove, MN (US)

(72) Inventors: Janel L. Lanphere, Flagstaff, AZ (US); John Spiridigliozzi, San Mateo, CA (US); Orla McCullagh, Maynard, MA (US); Paul DiCarlo, Middleboro, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 1150 days.

(21) Appl. No.: 13/628,892

(22) Filed: Sep. 27, 2012

(65) Prior Publication Data

US 2014/0088669 A1  Mar. 27, 2014

Related U.S. Application Data

(62) Division of application No. 12/761,054, filed on Apr. 15, 2010, now abandoned, which is a division of application No. 11/763,602, filed on Jun. 15, 2007, now abandoned.

(60) Provisional application No. 60/820,503, filed on Jul. 27, 2006.

(51) Int. Cl.
| *A61B 18/18* | (2006.01) |
| *A61K 33/14* | (2006.01) |
| *A61K 31/734* | (2006.01) |
| *A61K 33/06* | (2006.01) |
| *A61K 31/75* | (2006.01) |
| *A61K 41/00* | (2020.01) |
| *A61B 18/14* | (2006.01) |
| *A61B 18/00* | (2006.01) |

(52) U.S. Cl.
CPC .......... *A61K 33/14* (2013.01); *A61B 18/1477* (2013.01); *A61B 18/1815* (2013.01); *A61K 31/734* (2013.01); *A61K 31/75* (2013.01); *A61K 33/06* (2013.01); *A61K 41/0052* (2013.01); *A61B 2018/00577* (2013.01); *A61B 2018/143* (2013.01); *A61B 2018/1425* (2013.01)

(58) Field of Classification Search
CPC ............ A61K 2300/00; A61K 41/0052; A61K 49/0419; A61N 5/02; A61N 5/022; A61N 5/0625
USPC ........................................... 607/96, 100–103
See application file for complete search history.

(56) References Cited

U.S. PATENT DOCUMENTS

| 4,897,255 A | 1/1990 | Fritzberg et al. |
| 5,733,925 A | 3/1998 | Kunz et al. |
| 6,368,658 B1 | 4/2002 | Schwarz et al. |

(Continued)

FOREIGN PATENT DOCUMENTS

| WO | WO 1995/09585 | 4/1995 |
| WO | WO 99/59556 | 11/1999 |

(Continued)

OTHER PUBLICATIONS

Jordan, Andreas et al., "The effect of thermotherapy using magnetic nanoparticles on rat malignant glioma," Journal of Neuro-Oncology, vol. 78, No. 1, pp. 7-14, May 2006.

(Continued)

*Primary Examiner* — Kaitlyn E Smith
*Assistant Examiner* — Yasamin Ekrami

(57) ABSTRACT

Particles and related methods are disclosed.

16 Claims, 23 Drawing Sheets

(56) References Cited

U.S. PATENT DOCUMENTS

| | | | |
|---|---|---|---|
| 6,629,947 B1 | 10/2003 | Sahatjian et al. | |
| 6,635,055 B1 | 10/2003 | Cronin | |
| 7,744,913 B2 * | 6/2010 | Noyes | A61K 51/12 424/422 |
| 2003/0185895 A1 | 10/2003 | Lanphere et al. | |
| 2003/0203985 A1 | 10/2003 | Baldwin et al. | |
| 2003/0233150 A1 | 12/2003 | Bourne et al. | |
| 2004/0076582 A1 | 4/2004 | DiMatteo et al. | |
| 2004/0091543 A1 | 5/2004 | Bell et al. | |
| 2004/0096662 A1 * | 5/2004 | Lanphere | A61F 2/0036 428/402 |
| 2004/0101564 A1 | 5/2004 | Rioux et al. | |
| 2004/0144395 A1 | 7/2004 | Evans et al. | |
| 2005/0004576 A1 | 1/2005 | Benderev et al. | |
| 2005/0070930 A1 | 3/2005 | Kammerer | |
| 2005/0095428 A1 | 5/2005 | DiCarlo et al. | |
| 2005/0107660 A1 | 5/2005 | Valtchev | |
| 2005/0124560 A1 * | 6/2005 | Sung | A61L 15/28 514/26 |
| 2005/0129775 A1 * | 6/2005 | Lanphere | A61K 9/0009 424/489 |
| 2005/0171510 A1 | 8/2005 | DiCarlo et al. | |
| 2005/0191331 A1 | 9/2005 | Hunter et al. | |
| 2005/0196449 A1 | 9/2005 | DiCarlo et al. | |
| 2005/0234291 A1 | 10/2005 | Gingras | |
| 2005/0238870 A1 | 10/2005 | Buiser et al. | |
| 2005/0249817 A1 | 11/2005 | Haik et al. | |
| 2005/0283040 A1 | 12/2005 | Greenhaigh | |
| 2006/0199010 A1 * | 9/2006 | DiCarlo et al. | 428/402.2 |
| 2006/0247610 A1 * | 11/2006 | Lanphere et al. | 606/21 |
| 2009/0182309 A1 * | 7/2009 | Muffly | A61M 39/1011 604/535 |
| 2011/0142936 A1 * | 6/2011 | Campbell | A61L 27/50 424/484 |

FOREIGN PATENT DOCUMENTS

| | | |
|---|---|---|
| WO | WO 2000/32241 | 6/2000 |
| WO | WO 2002/062271 | 8/2002 |
| WO | WO 2004/064921 | 8/2004 |
| WO | WO 2005/034912 | 4/2005 |
| WO | WO 2006/093969 | 9/2006 |
| WO | WO 2006/125452 | 11/2006 |
| WO | WO 2008/014060 | 1/2008 |

OTHER PUBLICATIONS

Lao, L. et al., "Magnetic & hydrogel composite materials for hyperthermia applications," Journal of Materials Science, Materials in Medicine, vol. 15, No. 10, pp. 1061-1064, Oct. 2004.

Invitation to Pay Additional Fees issued by the EPO on Oct. 2, 2008 in the PCT application No. PCT/US2007/071299, filed on Jun. 15, 2007.

Sato et al., IEEE Transactions on Magnetics, vol. 29, No. 6, Nov. 1993; pp. 3325-3330.

* cited by examiner

PARTICLES

CROSS-REFERENCE TO RELATED APPLICATION

This application is a divisional of U.S. patent application Ser. No. 12/761,054 filed Apr. 15, 2010, which is a divisional of U.S. patent application Ser. No. 11/763,602 filed Jun. 15, 2007, now abandoned, which claims priority under 35 U.S.C. § 119 to U.S. Ser. No. 60/820,503, filed Jul. 27, 2006, the contents of which are hereby incorporated by reference.

FIELD

The invention relates to particles and related methods.

BACKGROUND

Ablation, such as radiofrequency (RF) ablation, can be used to treat pathological conditions in situ. For example, ablation can be used to treat a tumor by heating the tumor tissue (e.g., causing cells in the tumor tissue to die). In some instances, tumor ablation can be achieved by inserting an RF electrode having tines at one end into the area of a tumor, deploying the tines, and activating the RF electrode so that RF energy flows through the tines and heats the tumor tissue.

SUMMARY

In one aspect, the invention features a particle having an impedance of at most 60 ohms (e.g., at most about 50 ohms, at most about 40 ohms) at an applied power of two Watts. The particle has a maximum dimension (e.g., a diameter) of at most about 3,000 microns.

In another aspect, the invention features a method of making a particle having an impedance of at most 60 ohms (e.g., at most about 50 ohms, at most about 40 ohms) at an applied power of two Watts. The method includes generating drops including a gelling precursor, and contacting the drops with a solution including a gelling agent.

In an additional aspect, the invention features a method of making a particle. The method includes generating drops including a gelling precursor, and contacting the drops with a solution including a gelling agent including a multivalent cation. The concentration of the gelling agent in the solution is more than about 10 percent.

In a further aspect, the invention features a method that includes disposing at least one particle (e.g., a plurality of particles) in a tissue of a subject and exposing the particle to radiation to heat the tissue. The particle has a maximum dimension (e.g., a diameter) of at most about 3,000 microns and an impedance of at most 60 ohms (e.g., at most about 50 ohms, at most about 40 ohms) at an applied power of two Watts.

In another aspect, the invention features a gel having an impedance of at most 60 ohms (e.g., at most about 50 ohms, at most about 40 ohms) at an applied power of two Watts. In some embodiments, the gel can be configured to fit within a lumen of a subject.

In an additional aspect, the invention features a method of making a gel, the method including contacting a gelling precursor with a solution including a gelling agent. The gel has an impedance of at most 60 ohms (e.g., at most about 50 ohms, at most about 40 ohms) at an applied power of two Watts. In certain embodiments, the gel can be configured to fit within a lumen of a subject.

In a further aspect, the invention features a method of making a gel, the method including contacting a gelling precursor with a solution including a gelling agent including a multivalent cation. The concentration of the gelling agent in the solution is more than about 10 percent. In some embodiments, the gel can be configured to fit within a lumen of a subject.

In another aspect, the invention features a method including disposing a gel in a tissue of a subject, and exposing the gel to radiation to heat the tissue. The gel has an impedance of at most 60 ohms (e.g., at most about 50 ohms, at most about 40 ohms) at an applied power of two Watts.

In an additional aspect, the invention features a method of forming a gel in a tissue of a subject. The method includes contacting a gelling precursor with a solution including a gelling agent in the tissue of the subject. The gel has an impedance of at most 60 ohms (e.g., at most about 50 ohms, at most about 40 ohms) at an applied power of two Watts.

In a further aspect, the invention features a method of forming a gel in a tissue of a subject. The method includes contacting a gelling precursor with a solution including a gelling agent in the tissue of the subject. The concentration of the gelling agent in the gelling agent solution is more than about 10 percent.

Embodiments can include one or more of the following.

In some embodiments, the particle and/or the gel can have an impedance of at most 60 ohms (e.g., at most about 55 ohms, at most about 50 ohms, at most about 45 ohms, at most about 40 ohms, at most about 35 ohms, at most about 30 ohms, at most about 25 ohms, at most about 20 ohms) at an applied power of two Watts.

The particle and/or the gel may include a ferromagnetic material, or may not include a ferromagnetic material.

In certain embodiments, the particle and/or the drops can include a gelling precursor (e.g., alginate). In some embodiments, the particle and/or the drops can include at least one polymer, such as at least one of the following polymers: polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyvinyl acetate, polyglycolic acids, and poly(lactic-co-glycolic) acids.

In certain embodiments, the particle can include a gel. In some embodiments, the particle can include a gelling precursor, such as alginate. In certain embodiments, the particle can include a therapeutic agent.

The particle can have a maximum dimension (e.g., a diameter) of at most about 3,000 microns. In certain embodiments, the particle can have a maximum dimension (e.g., a diameter) of from about 100 microns to about 700 microns.

In some embodiments, the concentration of the gelling agent in the solution can be more than about 15 percent (e.g., more than about 20 percent, more than about 25 percent, more than about 30 percent, more than about 35 percent, more than about 40 percent).

In certain embodiments, the multivalent cation can be a calcium cation. In some embodiments, the gelling agent can be calcium chloride.

Heating the tissue can include ablating the tissue. In some embodiments, the method can include heating the tissue to a temperature of at least about 40° C. (e.g., more than about 46° C.) and/or at most about 200° C. For example, the method may include heating the tissue to a temperature of from about 42° C. to about 46° C. In certain embodiments, the method can include increasing the temperature of the tissue by at least about 3° C., and/or by at least about eight percent. In some embodiments, the tissue may include a tumor. In certain embodiments, the method can include exposing the particle to RF radiation and/or microwave radiation.

In some embodiments, the method can include disposing a plurality of particles in a tissue of a subject. The method can further include forming a pattern (e.g., a circle) out of the particles.

In some embodiments, disposing at least one particle in a tissue of a subject can include disposing a composition including the particle and a carrier fluid in the tissue of the subject. The carrier fluid can include saline, a contrast agent, calcium chloride, and/or water for injection (WFI). In certain embodiments, the particle can be disposed in the tissue of the subject by percutaneous injection.

In some embodiments, disposing a gel in a tissue of a subject can include forming the gel in the tissue of the subject.

Embodiments can include one or more of the following advantages.

In some embodiments, a particle can be used to enhance tissue heating and/or ablation procedures. For example, a particle with a relatively low impedance (e.g., lower than the impedance of tissue surrounding the particle) can be used to control the transmission of RF radiation through tissue, and/or to help transmit RF radiation to a specific location in a target site. In certain embodiments, the particle may be used to transmit RF radiation over a longer distance than the RF radiation would travel in the absence of the particle. In some embodiments, multiple particles with relatively low impedances may be delivered to specific locations at or near a target site, and may be used to control the transmission of RF radiation at or near the target site.

In some embodiments, multiple particles with relatively low impedances can be relatively uniformly distributed throughout and/or on top of a target site. For example, the particles can be delivered to specific locations in cancerous tissue, causing the particles to be relatively uniformly distributed throughout the cancerous tissue. A relatively uniform distribution of the particles at a target site can provide for a relatively even and consistent ablation of the target site. In certain embodiments, multiple particles can be used to form a pattern (e.g., a circle) at or near a target site. The pattern may provide for a relatively uniform and/or controlled distribution of RF radiation through the target site. For example, in some embodiments in which the particles are used to form a circle at a target site, the tines of an RF electrode can be delivered into the circle and activated, and the particles can transmit the RF radiation radially away from the circle, to a relatively uniform distance.

In some embodiments, the use of a particle with a relatively low impedance in a tissue heating and/or ablation procedure can result in a relatively short procedure time. For example, the particle may accelerate the distribution of RF radiation at a target site (e.g., within tissue of a subject) by helping to transmit RF radiation away from an RF electrode and to relatively far distances in the target site.

In some embodiments, a particle can be used to deliver one or more therapeutic agents (e.g., drugs) to a target site relatively efficiently and effectively. For example, during and/or after delivery to a target site, the particle can release one or more therapeutic agents. In certain embodiments, a particle can be used both to enhance tissue heating and/or ablation procedures, and to provide one or more therapeutic agents to a target site. For example, a particle that includes a therapeutic agent can also have a relatively low impedance. When the particle reaches a target site, the particle can release the therapeutic agent to the target site, and can be used in a tissue heating and/or ablation procedure at the target site.

Other aspects, features, and advantages are in the description, drawings, and claims.

DETAILED DESCRIPTION

Figure 1:
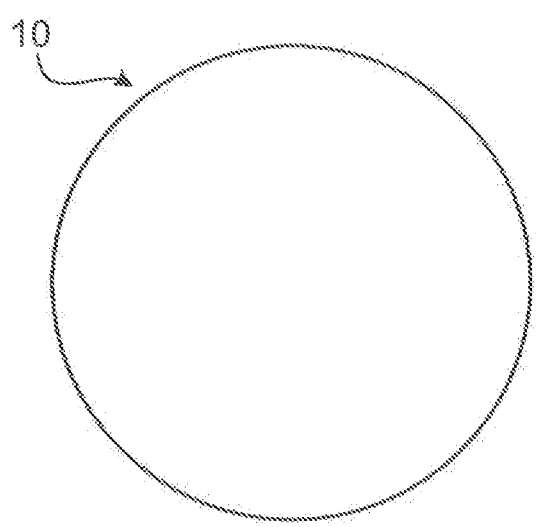
FIG. 1 is a side view of an embodiment of a particle.

FIG. 1 shows a particle 10 which has a relatively low impedance. Particles having a relatively low impedance can be desirable for use in, for example, a tissue heating and/or ablation procedure. In some embodiments, particles having a relatively low impedance can enhance a tissue heating and/or ablation procedure by transmitting RF radiation from an RF electrode through the tissue.

In certain embodiments, particle 10 can have an impedance of at most 60 ohms (e.g., at most about 55 ohms, at most about 50 ohms, at most about 45 ohms, at most about 40 ohms, at most about 35 ohms, at most about 30 ohms, at most about 25 ohms, at most about 20 ohms, at most about 15 ohms, at most about 10 ohms) at an applied power of at least about two Watts (e.g., two Watts, five Watts, 20 Watts). As referred to herein, the impedance of a particle is measured as follows. A mixture including sodium chloride solution (formed of sodium chloride dissolved in deionized water) and multiple particles of the same type is drained to remove most of the sodium chloride solution, leaving the particles densely packed and just covered by the sodium chloride solution. Two milliliters of the particle mixture are then added into a small vial. Two copper wires are used to connect the contents of the vial to an RF 3000® Generator (from Boston Scientific Corp.), with one end of each copper wire being submerged in the particle mixture and clipped to the side of the vial by an alligator clip, and the other end of each copper wire being attached to the RF generator by an alligator clip. The copper wires are attached to the vial at a fixed distance of 53.4 millimeters from each other. After the copper wires have been attached to the vial and the generator, the generator is started and the power level is selected. In some embodiments, the power that is applied while measuring the impedance of a particle or particles can be at least about two Watts (e.g., two Watts, five Watts, 20 Watts). The selected power is applied to the particles for a period of about five to 10 seconds, at which point the generator displays the impedance value for the particles at the selected applied power.

In some embodiments, a particle such as particle 10 can be used to enhance tissue heating and/or an ablation procedure. For example, FIGS. 2A-2F illustrate the use of a plurality of particles 10 in an ablation procedure that involves the exposure of unhealthy tissue to RF energy to damage or destroy the unhealthy tissue.

Figure 2A:
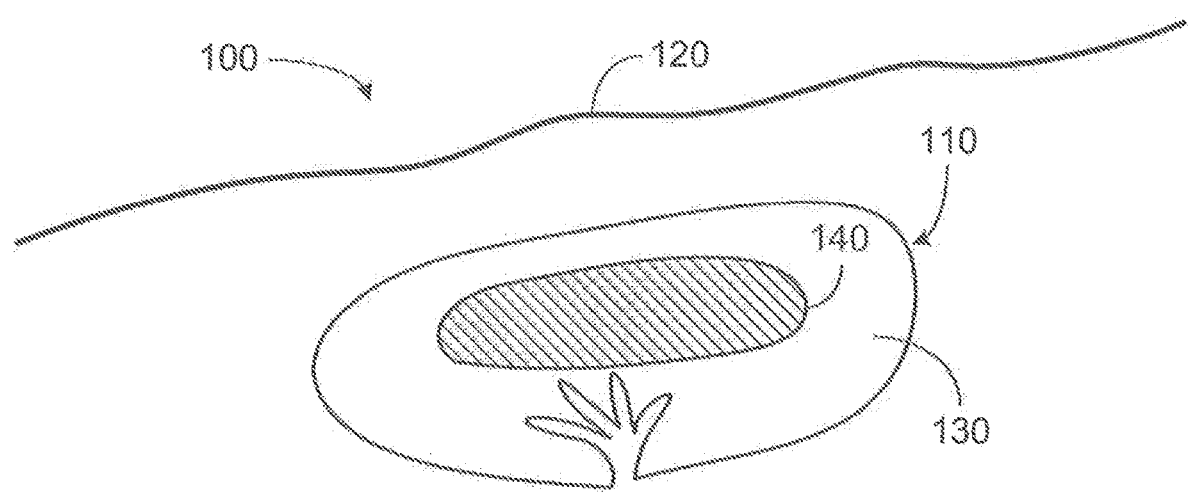
FIG. 2A is a cross-sectional view of a cancerous liver of a subject.

FIG. 2A shows a portion 100 of a subject including a liver 110 and skin 120. Liver 110 includes healthy tissue 130 and unhealthy tissue 140 (e.g., cancerous tissue, such as a cancerous tumor).

Figure 2B:
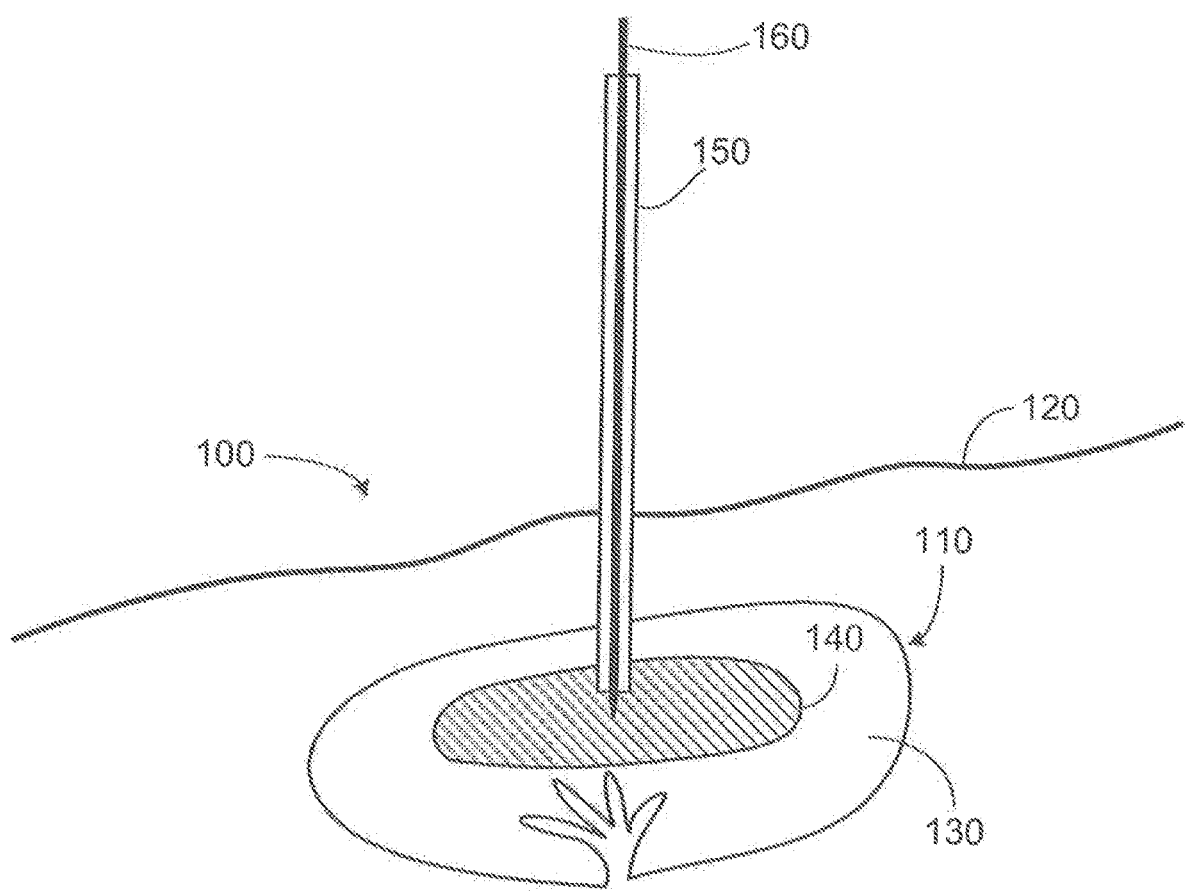
FIG. 2B illustrates delivery of an embodiment of a cannula into the liver of FIG. 2A.
Figure 2C:
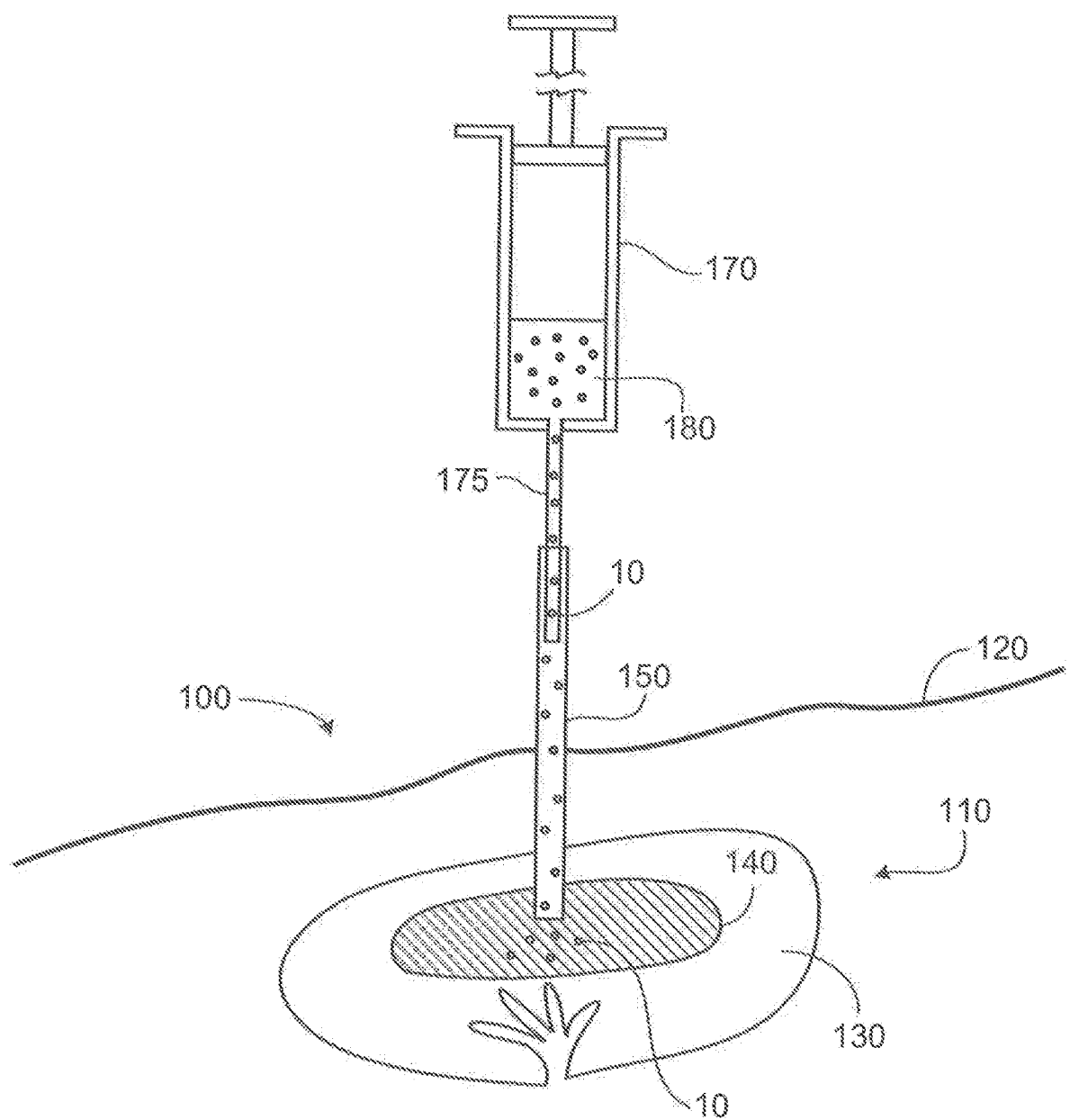
FIG. 2C illustrates administration of a plurality of FIG. 1 particles into the liver of FIG. 2A.
Figure 2D:
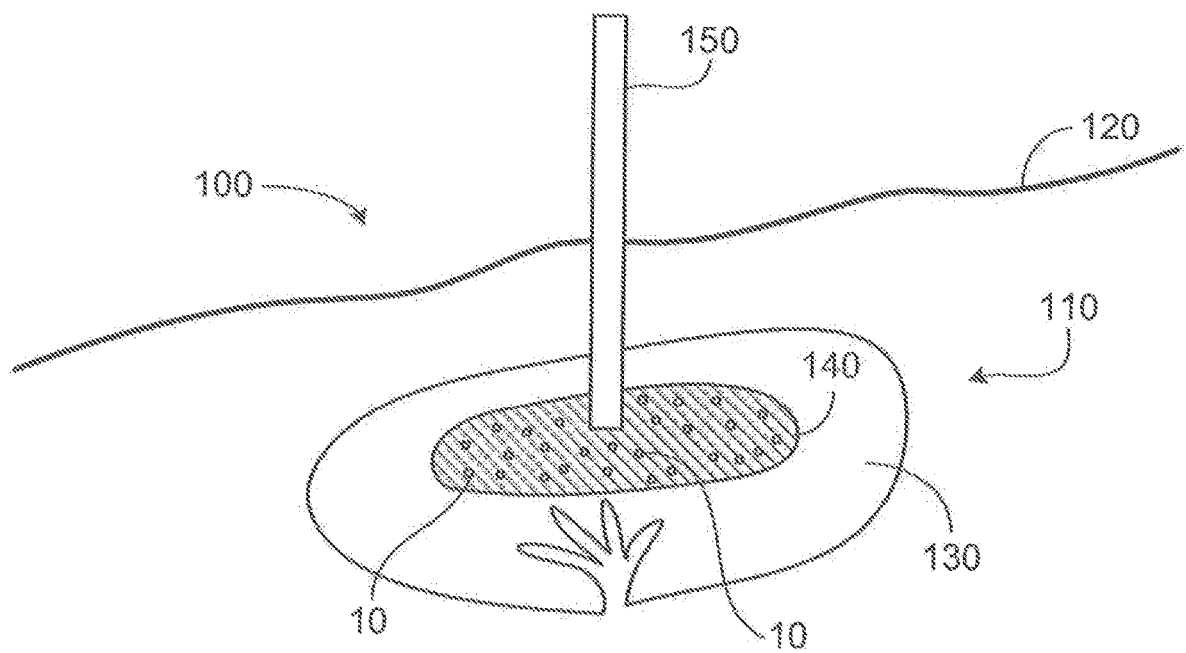
FIG. 2D is a cross-sectional view of the liver of FIG. 2A, after the particles have been administered into the liver.

FIG. 2B illustrates the delivery of a cannula 150 into unhealthy tissue 140, using a trocar 160. After cannula 150 has been delivered into unhealthy tissue 140, trocar 160 is removed from cannula 150 and, as shown in FIG. 2C, a needle 175 is inserted into cannula 150. Needle 175 is in fluid communication with a syringe 170, which contains a composition including particles 10 suspended in a carrier fluid 180. Particles 10 and carrier fluid 180 are injected from syringe 170, through needle 175 and cannula 150, and into unhealthy tissue 140. As shown in FIG. 2D, after particles 10 and carrier fluid 180 have been delivered into unhealthy tissue 140, needle 175 is removed from cannula 150.

In certain embodiments, particles 10 may not be suspended in a carrier fluid. For example, particles 10 alone can be contained within syringe 170, and injected from syringe 170 into unhealthy tissue 140.

While embodiments have been described in which a needle and cannula are used to deliver particles 10 into unhealthy tissue 140, in some embodiments, other delivery devices can be used to deliver particles 10 into unhealthy tissue 140. As an example, particles 10 can be delivered into unhealthy tissue 140 directly from a syringe. As another example, particles 10 can be delivered into unhealthy tissue 140 using a catheter. Alternatively or additionally, particles 10 can be delivered into unhealthy tissue 140 using other kinds of techniques. For example, an incision can be made in the subject to gain access to unhealthy tissue 140, and particles 10 can be deposited directly into unhealthy tissue 140 through the incision.

Figure 2E:
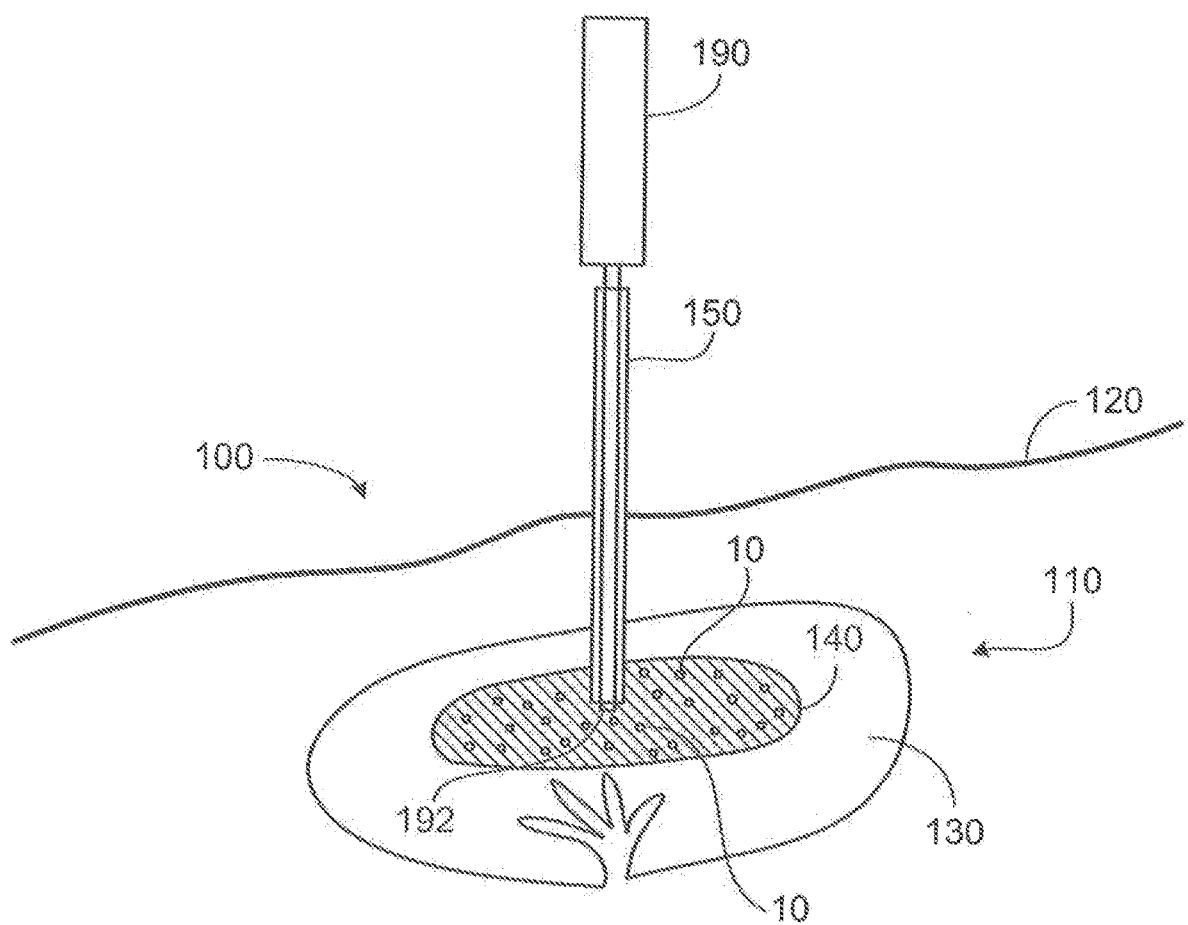
FIG. 2E illustrates delivery of an embodiment of an RF electrode into the liver of FIG. 2A.

FIG. 2E illustrates a method of treating unhealthy tissue 140 containing particles 10 with RF energy using a coaxial RF electrode system including a cannula 150 and a coaxial RF electrode 190 (e.g., a 3.5 centimeter coaxial electrode, such as the LeVeen CoAccess™ Electrode System (Boston Scientific Corp.)).

Figure 2F:
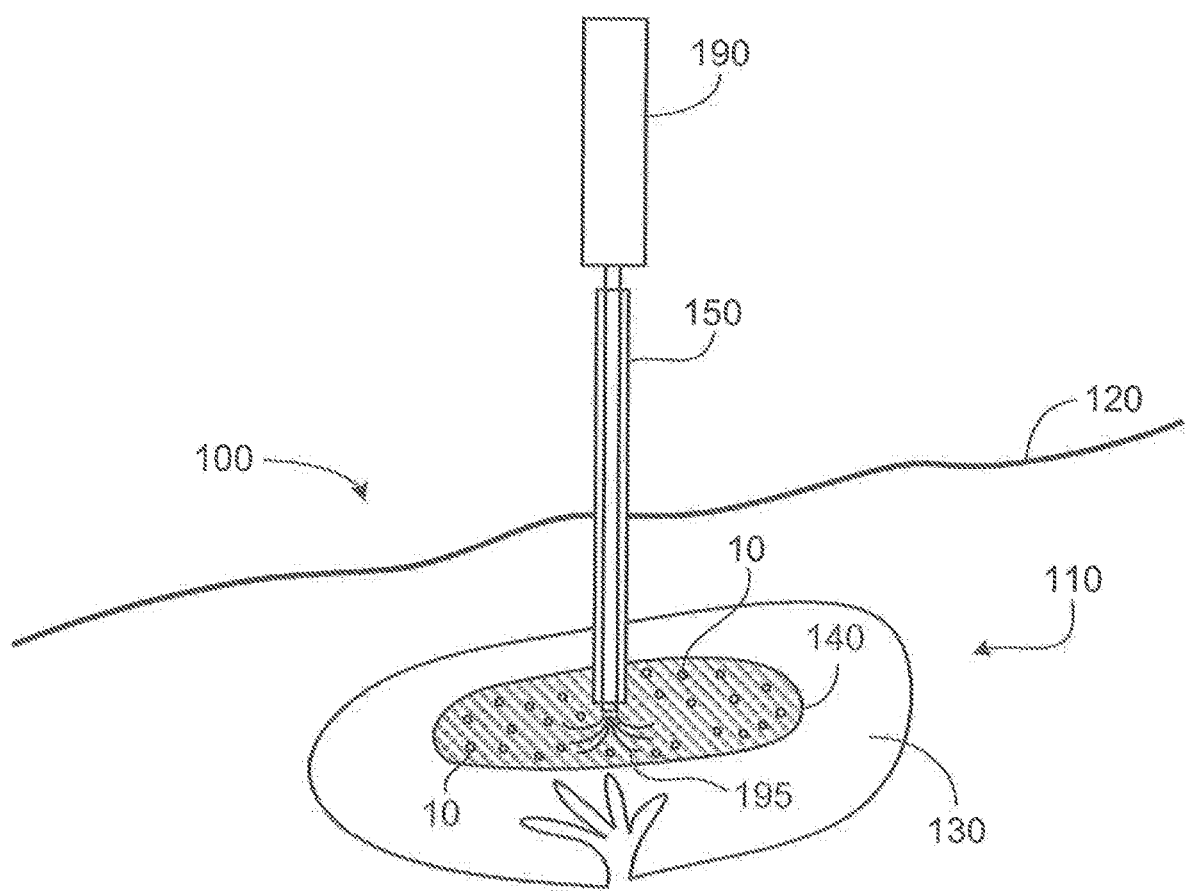
FIG. 2F illustrates an embodiment of an RF electrode with tines deployed within the cancerous tissue region of the liver of FIG. 2A.

As shown, RF electrode 190, which is an array electrode, is inserted into cannula 150, such that a distal end 192 of RF electrode 190 enters unhealthy tissue 140. As shown in FIG. 2F, after RF electrode 190 has been positioned within unhealthy tissue 140, tines 195 of RF electrode 190 are deployed within unhealthy tissue 140. In some embodiments, the maximum distance between RF electrode 190 (e.g., a tine 195 of RF electrode 190) and a particle 10 can be at most about 10 centimeters (e.g., at most about eight centimeters, at most about five centimeters, at most about two centimeters).

In certain embodiments, the distance between a component (e.g., a tine 195) of RF electrode 190 and a particle 10 can be selected based on the size of RF electrode 190. In some embodiments, as the size of RF electrode 190 increases, the selected distance between a component of RF electrode 190 and a particle 10 can increase. As an example, in certain embodiments, RF electrode 190 can be a two-centimeter electrode, so that when tines 195 are deployed, they can define an area having a maximum dimension of about two centimeters. In some embodiments in which RF electrode 190 is a two-centimeter electrode, the maximum distance between a component of RF electrode 190 and a particle 10 can be at most about five centimeters. As another example, in certain embodiments, RF electrode 190 can be a five-centimeter electrode, so that when tines 195 are deployed, they can define an area having a maximum dimension of about five centimeters. In some embodiments in which electrode 190 is a five-centimeter electrode, the maximum distance between a component of RF electrode 190 and a particle 10 can be at most about 12 centimeters.

RF electrode 190 can subsequently be activated so that RF energy is emitted from tines 195. The RF energy emitted from tines 195 can heat unhealthy tissue 140 around tines 195 to treat (e.g., ablate, damage, destroy) portions of unhealthy tissue 140 that are exposed to the energy.

In some embodiments, the RF energy emitted from tines 195 can heat unhealthy tissue 140 to a temperature of at least about 40° C. (e.g., at least about 42° C., at least about 46° C., at least about 50° C., at least about 75° C., at least about 100° C., at least about 125° C., at least about 150° C., at least about 175° C.), and/or at most about 200° C. (e.g., at most about 175° C., at most about 150° C., at most about 125° C., at most about 100° C., at most about 75° C., at most about 50° C., at most about 46° C., at most about 42° C.). In certain embodiments, the RF energy emitted from tines 195 can heat unhealthy issue 140 to a temperature of more than about 46° C.

In some embodiments, the temperature of unhealthy tissue 140 can increase by at least about 3° C. (e.g., at least about 5° C., at least about 9° C., at least about 13° C., at least about 38° C., at least about 63° C., at least about 88° C., at least about 113° C., at least about 138° C.), and/or at most about 163° C. (e.g., at most about 138° C., at most about 113° C., at most about 88° C., at most about 63° C., at most about 38° C., at most about 13° C., at most about 9° C., at most about 5° C.) during an ablation procedure.

In certain embodiments, the temperature of unhealthy tissue 140 can increase by at least about eight percent (e.g., at least about 10 percent, at least about 15 percent, at least about 25 percent, at least about 35 percent, at least about 50 percent, at least about 75 percent, at least about 100 percent, at least about 150 percent, at least about 170 percent, at least about 200 percent, at least about 240 percent, at least about 300 percent, at least about 370 percent, at least about 400 percent) and/or at most about 450 percent (e.g., at most about 400 percent, at most about 370 percent, at most about 300 percent, at most about 240 percent, at most about 200 percent, at most about 170 percent, at most about 150 percent, at most about 100 percent, at most about 75 percent, at most about 50 percent, at most about 35 percent, at most about 25 percent, at most about 15 percent, at most about 10 percent) during an ablation procedure.

Various algorithms can be used when exposing the particles to RF energy. Typically, the RF power source can be initially set at a certain power level, which can then be increased (e.g., monotonically) over time. In some embodiments, the RF power source is initially set at a power level of 30 Watts, and the power is increased by 10 Watts every minute. In certain embodiments, the RF power source is initially set at a power level of 60 Watts, and the power is increased by 10 Watts every 30 seconds. The end of the procedure can be determined, for example, by the temperature of the ablated tissue and/or by the measured impedance of the RF power circuit.

Without wishing to be bound by theory, it is believed that the presence of particles 10 in unhealthy tissue 140 may enhance the ablation of unhealthy tissue 140 (which can result in damage or destruction of the tissue) by RF electrode 190. In some embodiments, particles 10 may have a lower impedance than unhealthy tissue 140. This relatively low impedance may allow particles 10 to transmit RF radiation from RF electrode 190 throughout a relatively large area of unhealthy tissue 140. In certain embodiments, the relatively low impedance of particles 10 may allow particles 10 to transmit RF radiation away from tines 195 of RF electrode 190 relatively quickly. This transmission of RF radiation away from tines 195 may cause RF electrode 190 to continue emitting RF radiation for a longer period of time than it would otherwise (e.g., because RF electrode 190 may sense a relatively low temperature at the target site). As a result, a relatively complete ablation may be obtained.

It may be desirable to use a coaxial RF electrode (e.g., RF electrode 190), during an ablation procedure involving particles because the RF electrode can be positioned at a target site using the same cannula (e.g., cannula 150) that is used to deliver the particles to the target site. Thus, the RF electrode can be relatively easily positioned within the vicinity of the particles (e.g., the RF electrode can be deployed at the exact location where the particles have been delivered).

While an ablation procedure using a coaxial RF electrode system has been described, in some embodiments, an ablation procedure may involve the use of a non-coaxial RF electrode, and/or may not involve the use of a cannula.

Figure 3A:
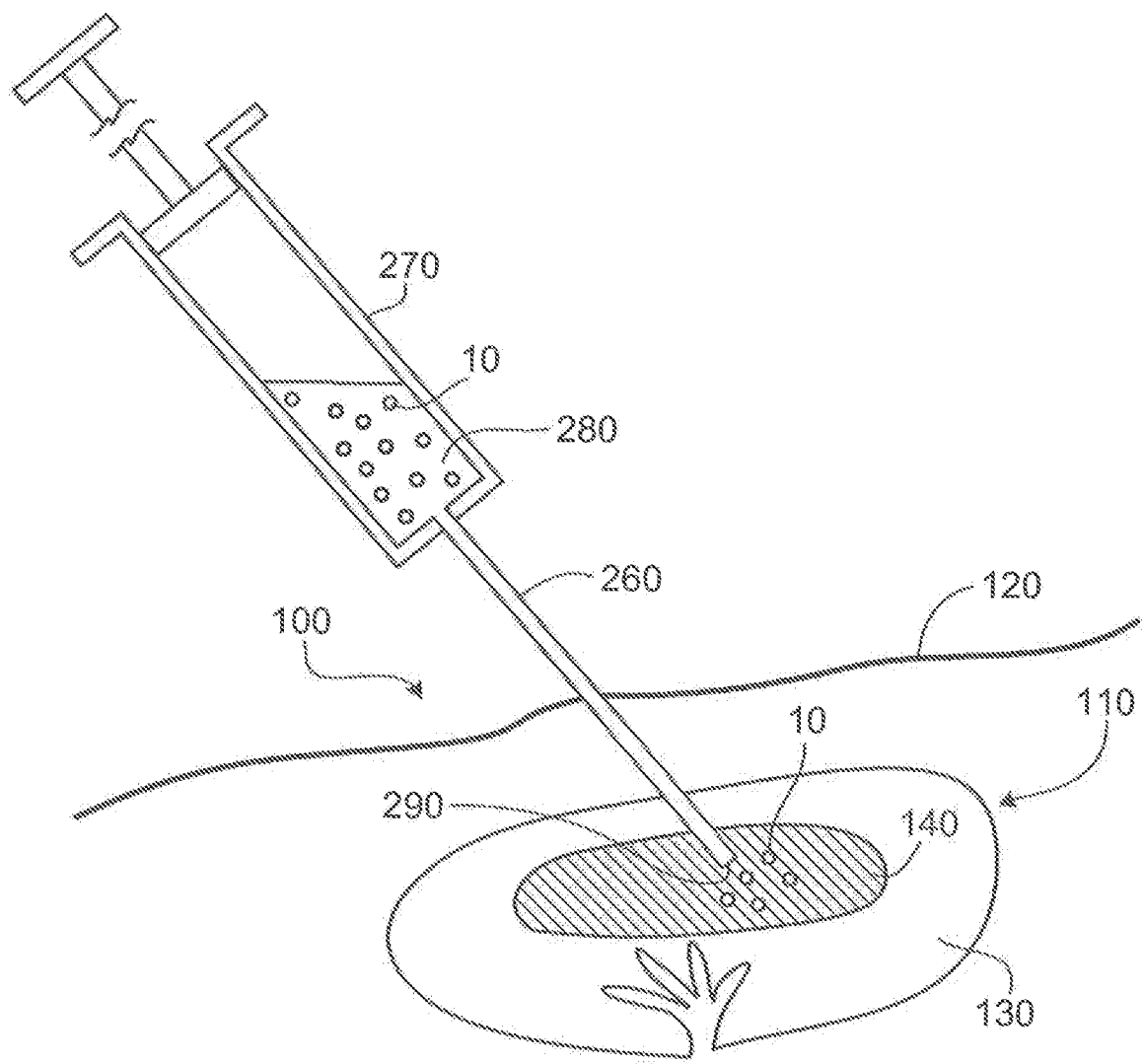
FIG. 3A illustrates administration of a plurality of FIG. 1 particles into the liver of FIG. 2A.
Figure 3B:
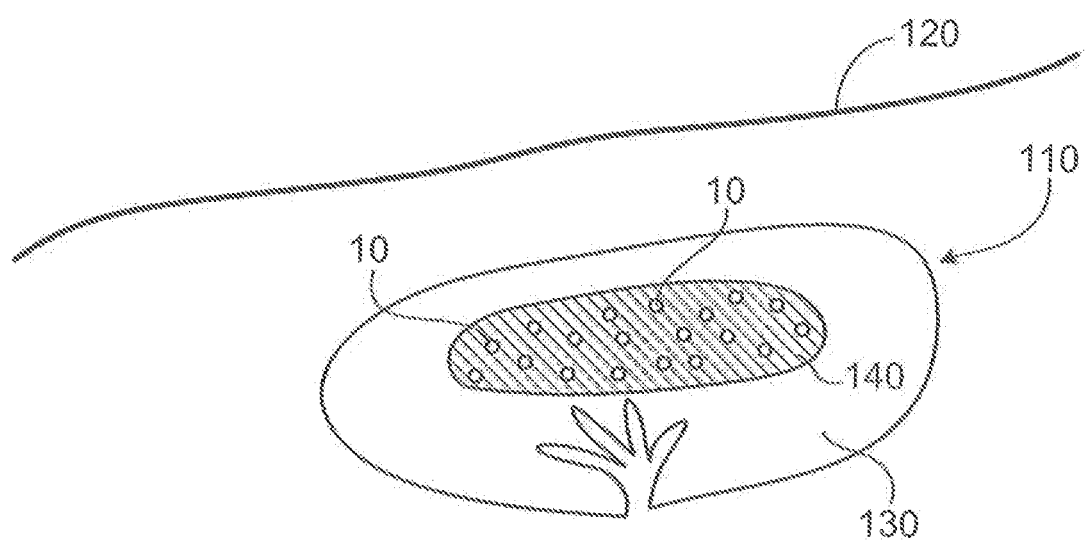
FIG. 3B is a cross-sectional view of the liver of FIG. 2A, after the particles have been administered into the liver.
Figure 3C:
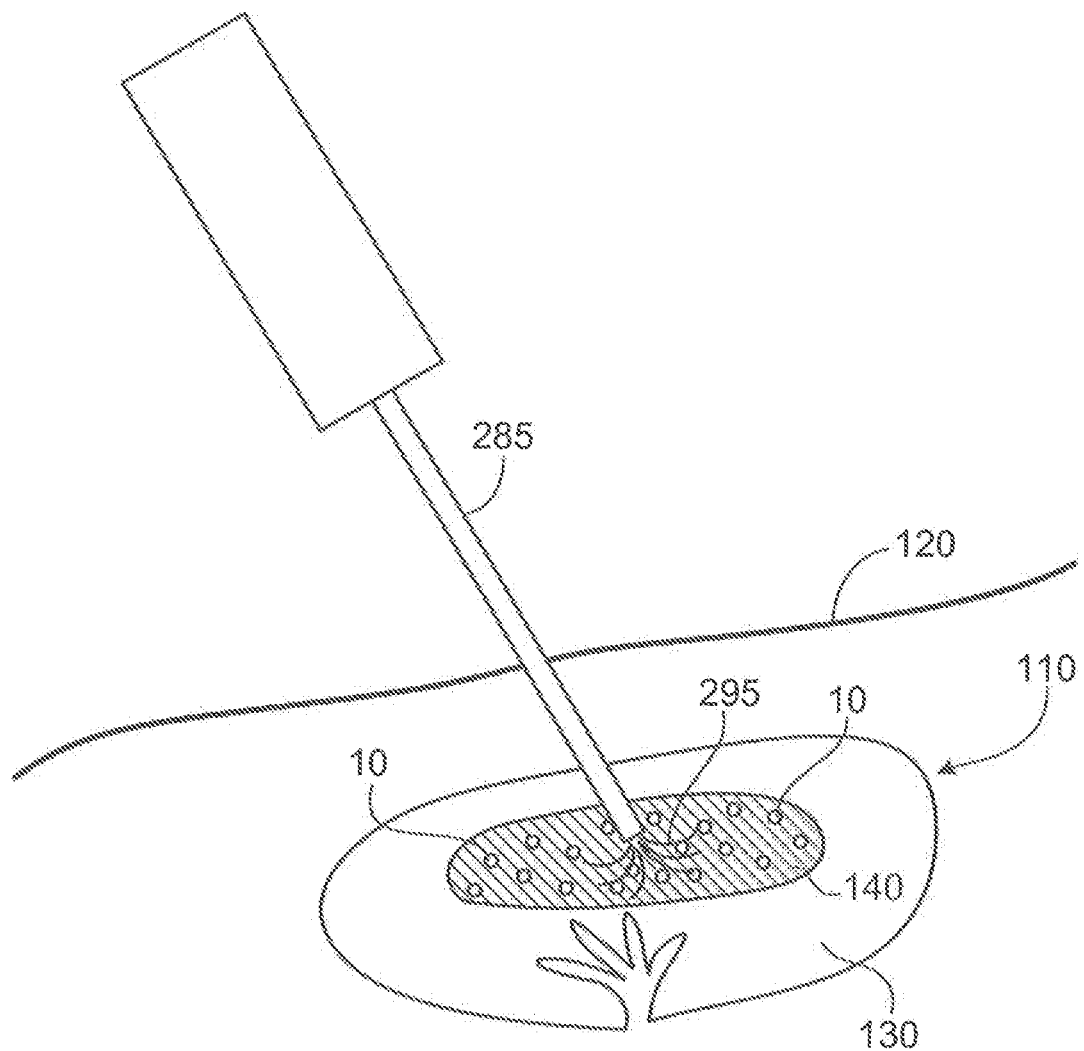
FIG. 3C illustrates an embodiment of an RF electrode with tines deployed within the cancerous tissue region of the liver of FIG. 2A.

For example, FIG. 3A illustrates the delivery of particles 10 into unhealthy tissue 140 of liver 110 using a needle 260. Needle 260 is in fluid communication with a syringe 270, which contains a composition including particles 10 suspended in a carrier fluid 280. An end 290 of needle 260 is inserted into unhealthy tissue 140, and particles 10 and carrier fluid 280 are injected from syringe 270 into unhealthy tissue 140, without using a cannula. As shown in FIG. 3B, after particles 10 and carrier fluid 280 have been delivered into unhealthy tissue 140, needle 260 is removed from unhealthy tissue 140. A non-coaxial RF electrode 285 is then positioned within unhealthy tissue 140 without using a cannula (e.g., by directly inserting RF electrode 285 through skin 120 of the subject). Examples of non-coaxial RF electrodes include the LeVeen Needle Electrode (Boston Scientific Corp.), the RITA StarBurst™ XL and the RITA StarBurst™ XLi (RITA® Medical Systems, Inc., Fremont, Calif.), and the Cool-tip™ RF Ablation System (Valleylab™, Boulder, Colo.). Once RF electrode 285 is positioned within unhealthy tissue 140, tines 295 of RF electrode 285 are deployed within unhealthy tissue 140, and RF electrode 285 is activated so that RF energy is emitted from tines 295.

In certain embodiments, particles such as particles 10 can be arranged (e.g., in a pattern) at a target site, such as unhealthy tissue 140 of liver 110, to further enhance tissue heating and/or ablation of the target site.

Figure 4A:
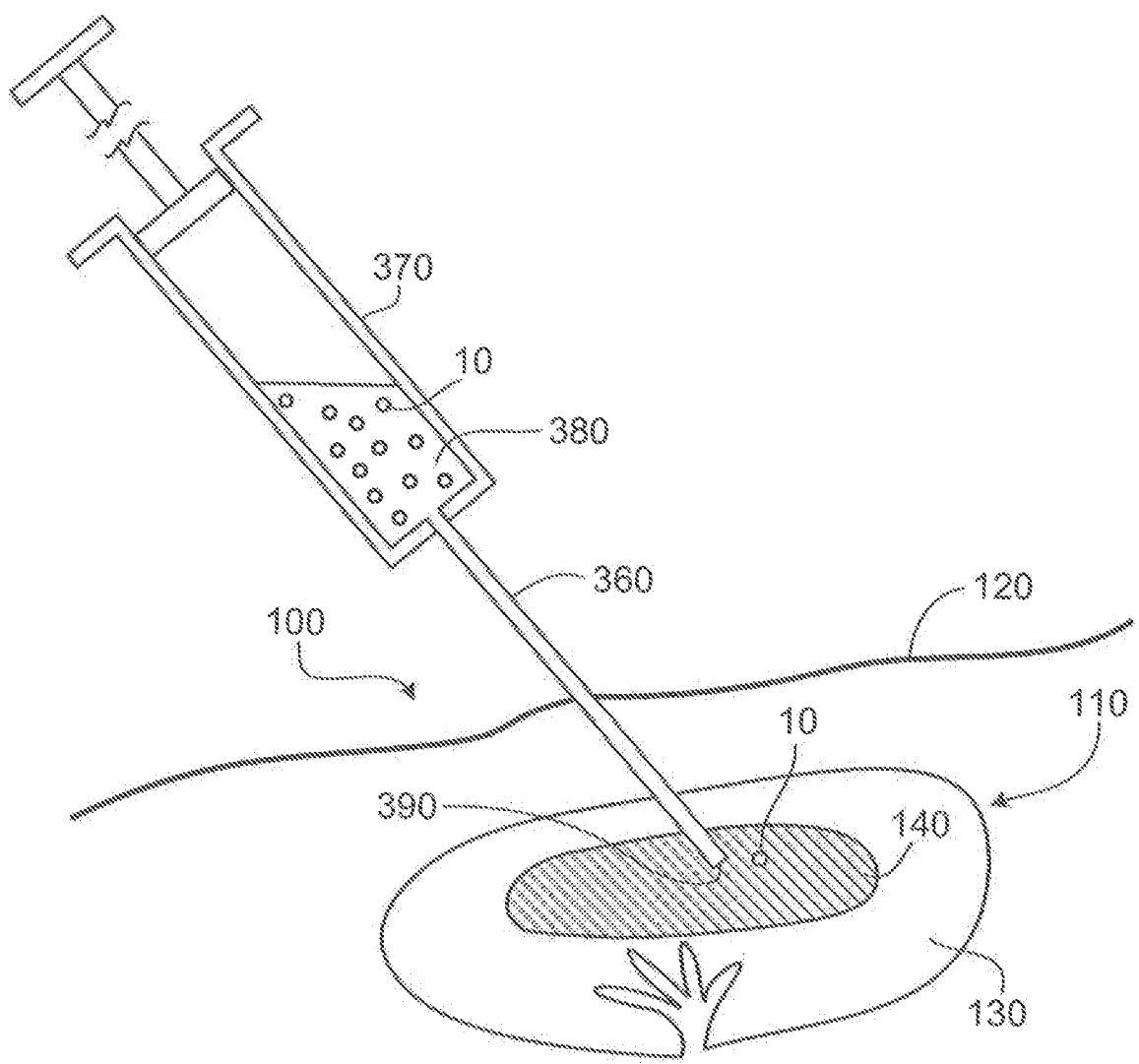
FIG. 4A illustrates administration of a plurality of FIG. 1 particles into the liver of FIG. 2A.
Figure 4B:
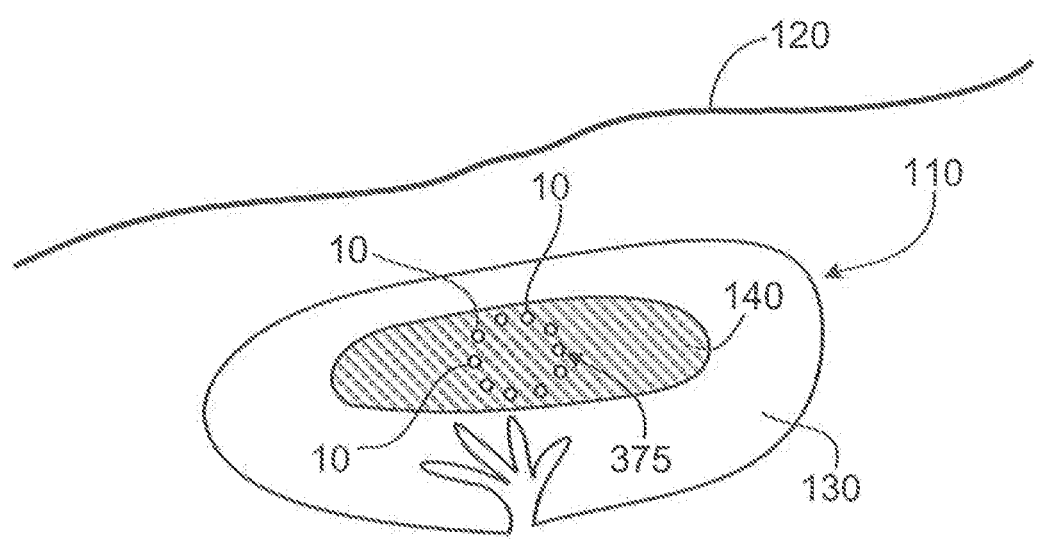
FIG. 4B is a cross-sectional view of the liver of FIG. 2A, after the particles have been administered into the liver.
Figure 4C:
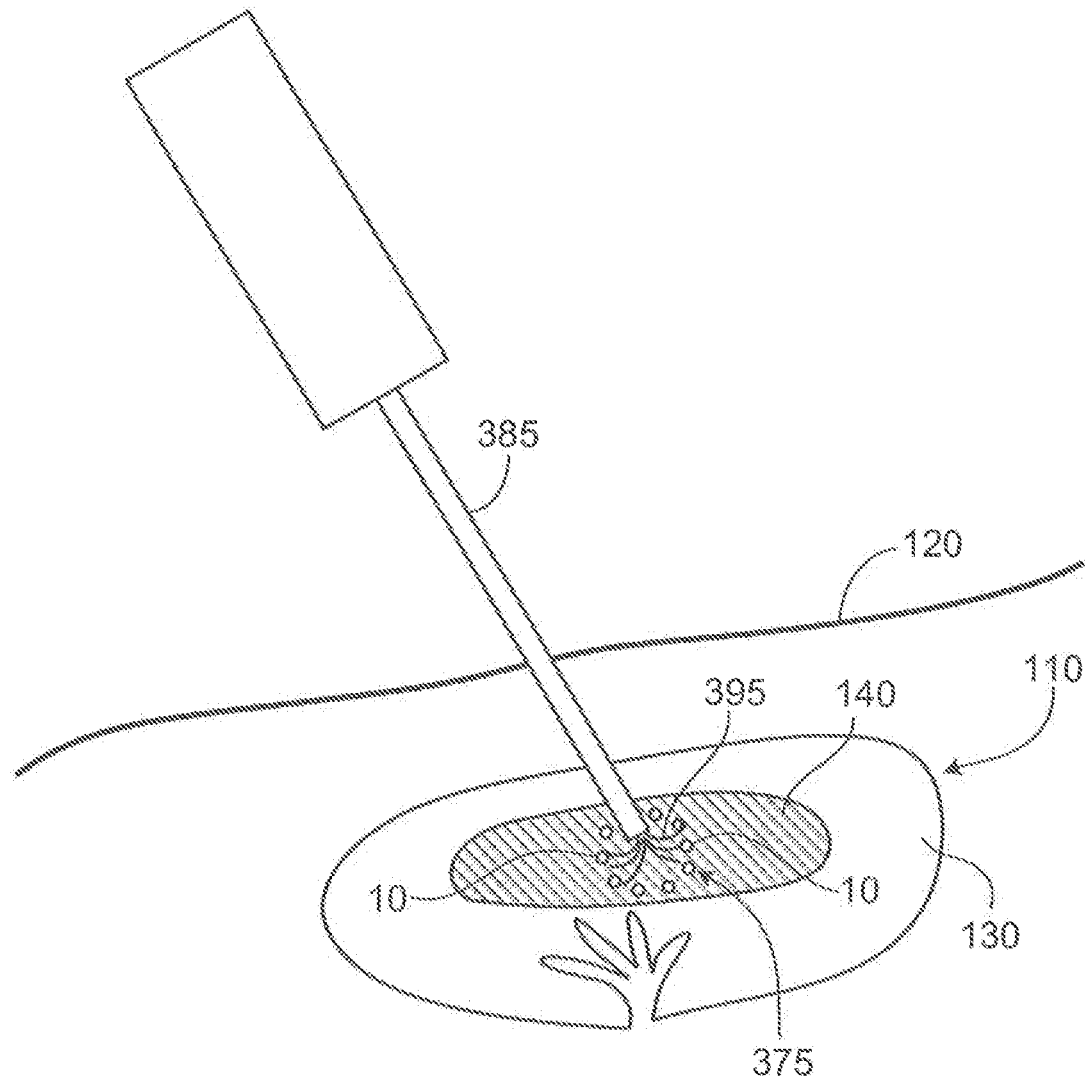
FIG. 4C illustrates an embodiment of an RF electrode with tines deployed within the cancerous tissue region of the liver of FIG. 2A.

For example, FIGS. 4A-4C illustrate the ablation of unhealthy tissue 140 of liver 110 using a pattern of particles 10. FIG. 4A shows the delivery of particles 10 into unhealthy tissue 140 of liver 110 using a needle 360. Needle 360 is in fluid communication with a syringe 370, which contains a composition including particles 10 suspended in a carrier fluid 380. An end 390 of needle 360 is inserted into unhealthy tissue 140, and particles 10 and carrier fluid 380 are then injected from syringe 370 into unhealthy tissue 140. During delivery of particles 10, a circle 375 of particles 10 is formed in unhealthy tissue 140 (FIG. 4B). Needle 360 is then removed from unhealthy tissue 140 and, as shown in FIG. 4C, an RF electrode 385 is positioned within unhealthy tissue 140. Tines 395 of RF electrode 385 are deployed within unhealthy tissue 140, inside of circle 375 of particles 10. RF electrode 385 is then activated so that RF energy is emitted from tines 395.

Without wishing to be bound by theory, it is believed that the use of a pattern of particles, such as circle 375 of particles 10, can help to relatively uniformly distribute RF energy at a target site. The relatively uniform distribution of RF energy at the target site can help in the formation of a relatively even and uniform burn at the target site. In some embodiments, the use of a pattern of particles at a target site can allow for the formation of a burn having a particular size and/or shape.

A particle such as particle 10 can include (e.g., can be formed of) one material or more than one material.

In some embodiments, a particle can include one or more polymers. Examples of polymers include polyvinyl alcohols (PVA), polyacrylic acids, polymethacrylic acids, poly vinyl sulfonates, carboxymethyl celluloses, hydroxyethyl celluloses, substituted celluloses, polyacrylamides, polyethylene glycols, polyamides (e.g., nylon), polyureas, polyurethanes, polyesters, polyethers, polystyrenes, polysaccharides (e.g., alginate, agarose), polylactic acids, polyethylenes, polymethylmethacrylates, polyethylacrylate, polycaprolactones, polyglycolic acids, poly(lactic-co-glycolic) acids (e.g., poly (d-lactic-co-glycolic) acids), and copolymers or mixtures thereof. In certain embodiments, the polymer can be a highly water insoluble, high molecular weight polymer. An example of such a polymer is a high molecular weight polyvinyl alcohol (PVA) that has been acetalized. The polymer can be substantially pure intrachain 1,3-acetalized PVA and substantially free of animal derived residue such as collagen.

In some embodiments, a particle can include one or more gelling precursors. Examples of gelling precursors include alginates, alginate salts (e.g. sodium alginate), xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. An example of sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which can produce a high tensile, robust gel.

In certain embodiments, a particle can include one or more polymers and one or more gelling precursors.

In some embodiments, a particle can include one or more bioerodible and/or bioabsorbable materials. In certain embodiments, a particle may be formed entirely of bioerodible and/or bioabsorbable materials. This can, for example, allow the particle to erode and/or to be absorbed after being used at a target site (e.g., in an ablation procedure). Examples of bioerodible and/or bioabsorbable materials include polysaccharides (e.g., alginate); polysaccharide derivatives; inorganic, ionic salts; water soluble polymers (e.g., polyvinyl alcohol, such as polyvinyl alcohol that has not been cross-linked); biodegradable poly DL-lactide-poly ethylene glycol (PELA); hydrogels (e.g., polyacrylic acid, hyaluronic acid, gelatin, carboxymethyl cellulose); polyethylene glycol (PEG); chitosan; polyesters (e.g., polycaprolactones); poly(lactic-co-glycolic) acid (e.g., a poly(d-lactic-co-glycolic) acid); and combinations thereof. In some embodiments, a particle can include sodium alginate.

In certain embodiments, a particle can include one or more gelled materials, and/or can be in a gel form. For example, a particle may be formed of a gelling precursor (e.g., alginate) that has been gelled by being contacted with a gelling agent (e.g., calcium chloride).

Figure 5:
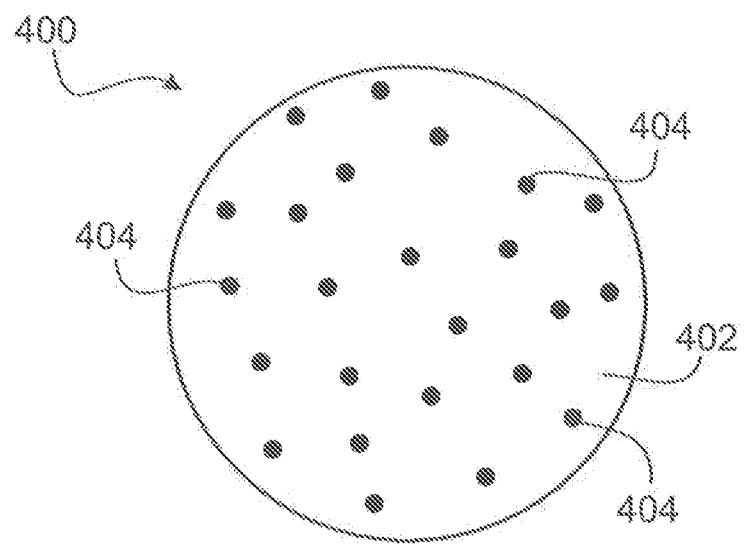
FIG. 5 is a cross-sectional view of an embodiment of a particle.
Figure 6:
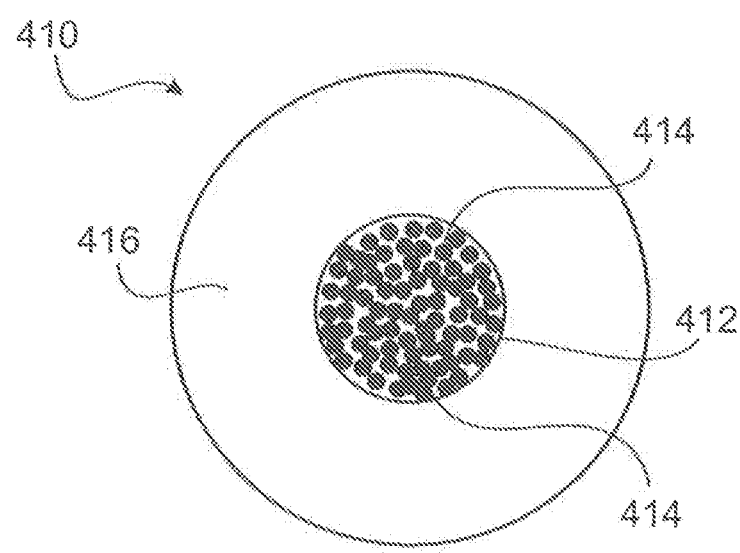
FIG. 6 is a cross-sectional view of an embodiment of a particle.

In some embodiments, a particle can include one or more ferromagnetic materials. For example, FIG. 5 shows a particle 400 that includes a polymer matrix 402 and ferromagnetic particles 404 dispersed throughout polymer matrix 402. FIG. 6 shows a particle 410 that has a cavity 412 containing ferromagnetic particles 414 and surrounded by a polymer matrix 416. Without wishing to be bound by theory, it is believed that the presence of one or more ferromagnetic materials in a particle may enhance the use of the particle in an ablation procedure. It is believed that when the particle is exposed to RF radiation, the ferromagnetic material in the particle can become heated, thereby heating the particle and, in turn, the target site (e.g., tissue).

A particle can include one type of ferromagnetic material, or multiple types of ferromagnetic materials. In some embodiments, a particle can include ferromagnetic particles that are formed of one type of ferromagnetic material, and ferromagnetic particles that are formed of a different type of ferromagnetic material. As used herein, a ferromagnetic material refers to a material that has a magnetic susceptibility of at least about 0.075 or more (e.g., at least about 0.1 or more; at least about 0.2 or more; at least about 0.3 or more; at least about 0.4 or more; at least about 0.5 or more; at least about one or more; at least about 10 or more; at least about 100 or more; at least about 1,000 or more; at least about 10,000 or more) when measured at 25° C. A ferromagnetic material can be, for example, a metal (e.g., a transition metal such as nickel, cobalt, or iron), a metal alloy (e.g., a nickel-iron alloy such as Mu-metal), a metal oxide (e.g., an iron oxide such as magnetite), a ceramic nanomaterial, a soft ferrite (e.g., nickel-zinc-iron), a magnet alloy (e.g., a rare earth magnet alloy such as a neodymium-iron-boron alloy or a samarium-cobalt alloy), an amorphous alloy (e.g., iron-silicon-boron), a non-earth alloy, or a silicon alloy (e.g., an iron-zirconium-copper-boron-silicon alloy, an iron-zirconium-copper-boron-silicon alloy). Iron oxide particles are commercially available from Micromod Partikeltechnologie GmbH (Friedrich-Barnewitz-Str.4 18119 Rostock-Warnemuende, Germany), under the tradename Micromod®. Magnetite is commercially available from FerroTec Corporation (Nashua, N.H.), under the tradename EMG 1111 Ferrofluid. Iron-copper-niobium-boron-silicon alloys are commercially available from Hitachi Metals of America under the tradename Finemet™. Iron-zirconium-copperboron-silicon alloys are commercially available from MAG-NETEC GmbH under the tradename Nanoperm®.

In some embodiments, a ferromagnetic material can be added to a particle by injection of the ferromagnetic material into the particle and/or by soaking the particle in the ferromagnetic material. Ferromagnetic materials are described, for example, in Rioux et al., U.S. Patent Application Publication No. US 2004/0101564 A1, published on May 27, 2004, and entitled "Embolization", and in Lanphere et al., U.S. Patent Application Publication No. US 2005/0129775 A1, published on Jun. 16, 2005, and entitled "Ferromagnetic Particles and Methods", both of which are incorporated herein by reference.

While particles that include ferromagnetic materials have been described, in certain embodiments, a particle may not include any ferromagnetic material. In some embodiments, a particle that does not include any ferromagnetic material may have a relatively low impedance (e.g., at most 60 ohms, at most about 55 ohms, at most about 50 ohms, at most about 45 ohms, at most about 40 ohms, at most about 35 ohms, at most about 30 ohms, at most about 25 ohms, at most about 20 ohms, at most about 15 ohms, at most about 10 ohms). In certain embodiments, a particle that does not include any ferromagnetic material may be used to enhance an ablation procedure (e.g., by having a relatively low impedance).

A particle (e.g., particle 10) can have any of a number of different shapes and/or sizes.

In certain embodiments, a particle can be substantially spherical. In some embodiments, a particle can have a sphericity of about 0.8 or more (e.g., about 0.85 or more, about 0.9 or more, about 0.95 or more, about 0.97 or more). In certain embodiments, the sphericity of a particle after compression in a delivery device such as a catheter (e.g., after compression to about 50 percent or more of the cross-sectional area of the particle) can be about 0.8 or more (e.g., about 0.85 or more, about 0.9 or more, about 0.95 or more, about 0.97 or more). The particle can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more).

The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where Da=¯√4A/n); Dp=P/it; A=pixel area; P=pixel perimeter), is a value from zero to one, with one representing a perfect circle.

In some embodiments, a particle can be substantially nonspherical. For example, a particle can be conical, diamond-shaped, spheroidal, cylindrical, or irregularly shaped. In certain embodiments, a particle can be mechanically shaped during or after the particle formation process to be nonspherical (e.g., ellipsoidal). In some embodiments, a particle can be shaped (e.g., molded, compressed, punched, and/or agglomerated with other particles) at different points in the particle manufacturing process. As an example, in certain embodiments in which a particle is formed using a gelling agent, the particle can be physically deformed into a specific shape and/or size after the particle has been contacted with the gelling agent, but before the polymer(s) in the particle have been cross-linked. After shaping, the polymer(s) (e.g., polyvinyl alcohol) in the particles can be cross-linked, optionally followed by substantial removal of gelling precursor (e.g., alginate). In some embodiments, a nonspherical particle can be formed by post-processing the particle (e.g., by cutting or dicing into other shapes). Particle shaping is described, for example, in Baldwin et al., U.S. Patent Application Publication No. US 2003/0203985 A1, published on Oct. 30, 2003, and entitled "Forming a Chemically Cross-Linked Particle of a Desired Shape and Diameter", which is incorporated herein by reference.

In general, a particle can have a maximum dimension (e.g., a diameter) of at most about 3,000 microns (e.g., from about two microns to about 3,000 microns, from about 10 microns to about 3,000 microns, from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns). In some embodiments, a particle can have a maximum dimension (e.g., a diameter) of at most about 3,000 microns (e.g., at most about 2,500 microns; at most about 2,000 microns; at most about 1,500 microns; at most about 1,200 microns; at most about 1,000 microns; at most about 900 microns; at most about 700 microns; at most about 500 microns; at most about 400 microns; at most about 300 microns; at most about 100 microns; at most about 10 microns; at most about five microns), and/or at least about two microns (e.g., at least about five microns; at least about 10 microns; at least about 100 microns; at least about 300 microns; at least about 400 microns; at least about 500 microns; at least about 700 microns; at least about 900 microns; at least about 1,000 microns; at least about 1,200 microns; at least about 1,500 microns; at least about 2,000 microns; at least about 2,500 microns).

In certain embodiments, a plurality of particles can have an arithmetic mean diameter of at most about 3,000 microns (e.g., at most about 2,500 microns; at most about 2,000 microns; at most about 1,500 microns; at most about 1,200 microns; at most about 900 microns; at most about 700 microns; at most about 500 microns; at most about 400 microns; at most about 300 microns; at most about 100 microns; at most about 10 microns; at most about five microns), and/or at least about two microns (e.g., at least about five microns; at least about 10 microns; at least about 100 microns; at least about 300 microns; at least about 400 microns; at least about 500 microns; at least about 700 microns; at least about 900 microns; at least about 1,200 microns; at least about 1,500 microns; at least about 2,000 microns; at least about 2,500 microns). Exemplary ranges for the arithmetic mean diameter of particles (e.g., particles delivered to a subject) include from about 100 microns to about 500 microns; from about 100 microns to about 300 microns; from about 300 microns to about 500 microns; from about 500 microns to about 700 microns; and from about 900 microns to about 1,200 microns. In general, the particles delivered to a subject in a composition can have an arithmetic mean diameter in approximately the middle of the range of the diameters of the individual particles, and a variance of at most about 20 percent (e.g., at most about 15 percent, at most about 10 percent).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

Figure 7:
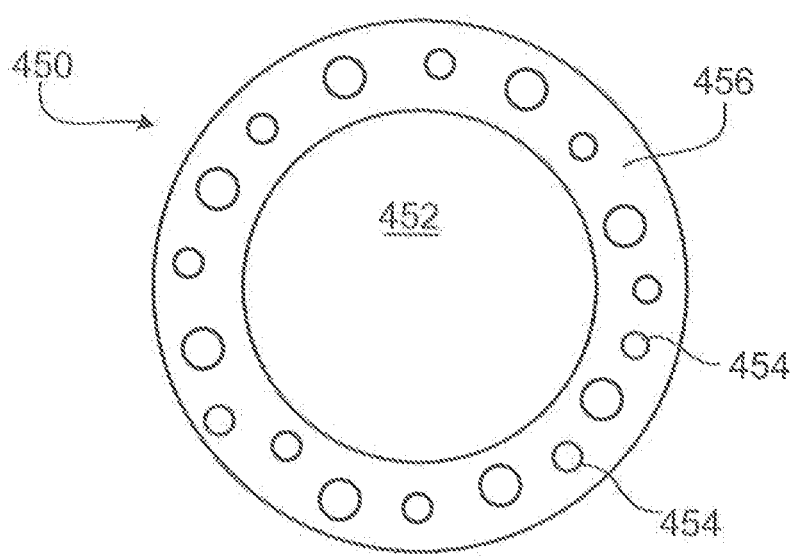
FIG. 7 is a cross-sectional view of an embodiment of a particle.

In certain embodiments, a particle such as particle 10 can be porous and/or can include at least one cavity (a hollow central region in the particle). In certain embodiments in which a particle includes a cavity, the particle can further include pores in the material surrounding the cavity. For example, FIG. 7 shows a particle 450 with a cavity 452 surrounded by a matrix material 456 (e.g., a polymer) that includes pores 454.

Figure 8:
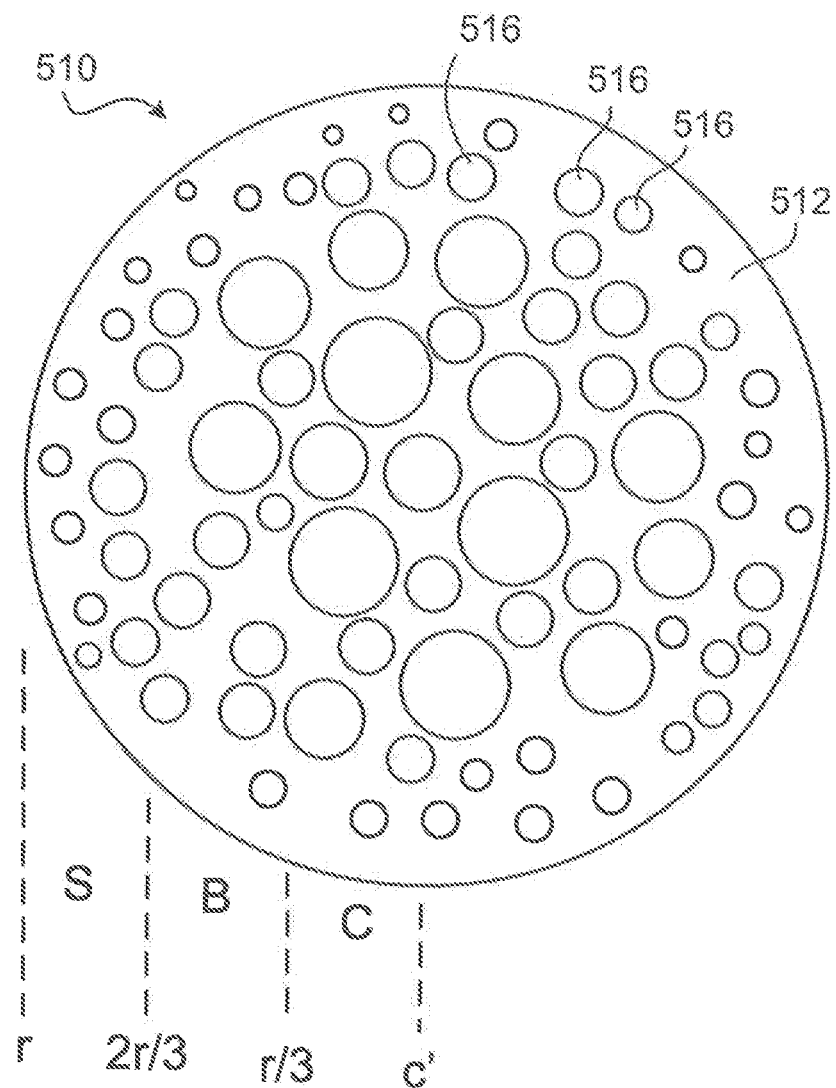
FIG. 8 is a cross-sectional view of an embodiment of a particle.

In some embodiments, a porous particle can have a particular distribution of pores. For example, FIG. 8 shows a particle 510 that can be considered to include a center region, C, from the center c' of particle 510 to a radius of about r/3, a body region, B, from about r/3 to about 2r/3, and a surface region, S, from about 2r/3 to r. The regions can be characterized by the relative size of pores 516 present in particle 510 in each region, the density of pores 516 (the number of pores 516 per unit volume of particle 510) in each region, and/or the mass density (the density of the matrix 512 and material 514 mass per unit volume of particle 510) in each region.

In general, the mean size of pores 516 in region C of particle 510 can be greater than the mean size of pores 516 at region S of particle 510. In some embodiments, the mean size of pores 516 in region C of particle 510 can be greater than the mean size of pores 516 in region B particle 510, and/or the mean size of pores 516 in region B of particle 510 can be greater than the mean size of pores 516 at region S particle 510. The size of pores 516 in particle 510 can be measured by viewing a cross-section of particle 510. For irregularly shaped (nonspherical) pores, the maximum visible cross-section is used.

Generally, the density of pores 516 in region C of particle 10 can be greater than the density of pores 516 at region S of particle 510. In some embodiments, the density of pores 516 in region C of particle 510 can be greater than the density of pores 516 in region B of particle 510, and/or the density of pores 516 in region B of particle 510 can be greater than the density of pores 516 at region S of particle 510.

In general, the mass density in region C of particle 510 can be less than the mass density at region S of particle 510. In some embodiments, the mass density in region C of particle 510 can be less than the mass density in region B of particle 510, and/or the mass density in region B of particle 510 can be less than the mass density at region S of particle 510.

Porous particles are described, for example, in Lanphere et al., U.S. Patent Application Publication No. US 2004/0096662 A1, published on May 20, 2004, and entitled "Embolization", which is incorporated herein by reference.

Particles such as particle 10 can be produced using any of a number of different methods.

Figure 9A:
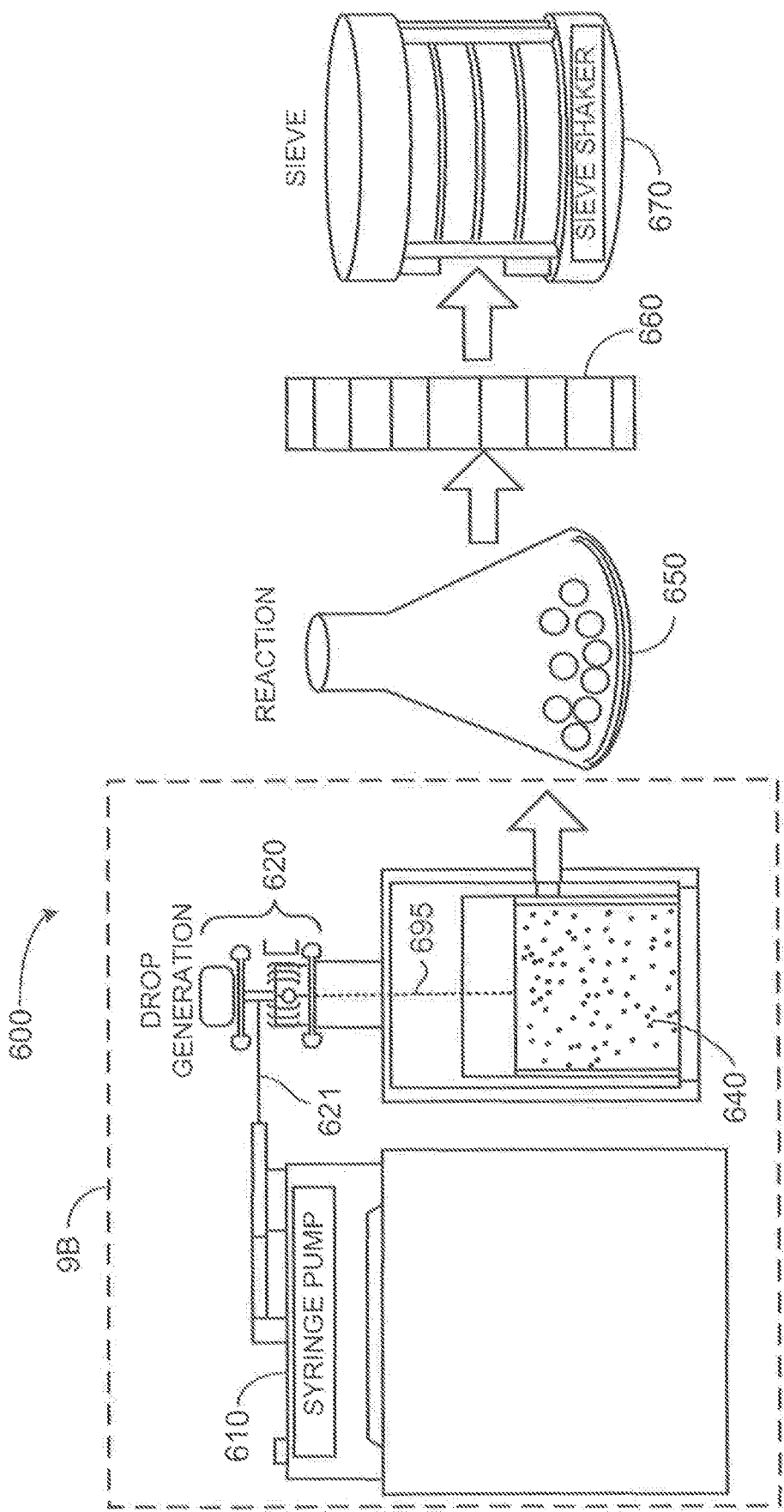
FIG. 9A is a schematic of an embodiment of a process for manufacturing particles.
Figure 9B:
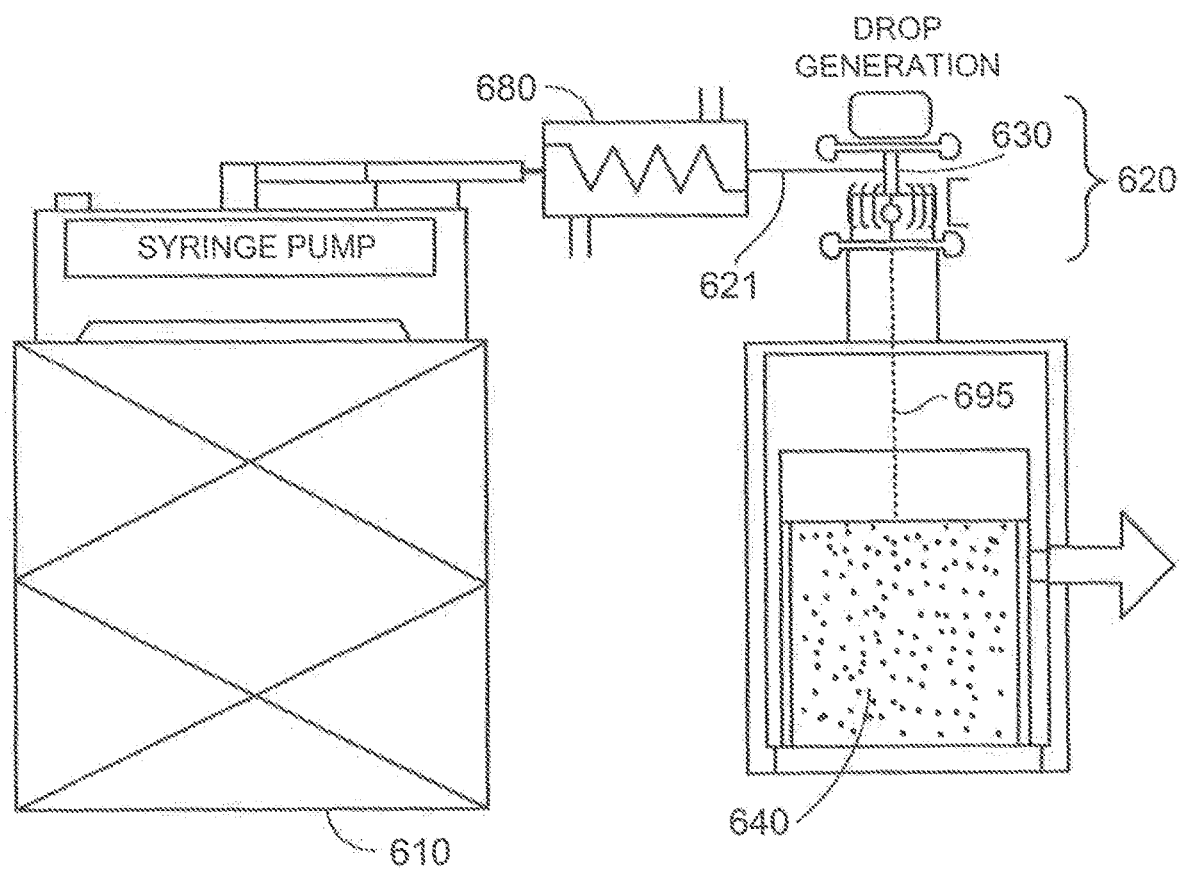
FIG. 9B is an enlarged schematic of region 9B in FIG. 9A.

As an example, FIGS. 9A and 9B show a system 600 for producing particles, such as particle 10. System 600 includes a flow controller 610, a drop generator 620 including a nozzle 630, a gelling vessel 640, a reactor vessel 650, an optional gel dissolution chamber 660, and a filter 670. An example of a commercially available drop generator is the model NISCO Encapsulation unit VAR D (NISCO Engineering, Zurich, Switzerland).

Flow controller 610 includes a high pressure pumping apparatus, such as a syringe pump (e.g., model PHD4400, Harvard Apparatus, Holliston, Mass.). Flow controller 610 delivers a stream of a solution including a polymer and a gelling precursor to a viscosity controller 680. In some embodiments, the solution can include up to eight percent by weight (e.g., up to 7.06 percent by weight) of the polymer and/or up to five percent by weight (e.g., from 1.76 percent by weight to five percent by weight) of the gelling precursor. Viscosity controller 680 heats the solution to reduce its viscosity prior to delivery to drop generator 620. Viscosity controller 680 is connected to nozzle 630 of drop generator 620 via tubing 621. After the stream of the solution has traveled from flow controller 680 through tubing 621, the stream flows into drop generator 620 and enters nozzle 630. As the stream nozzle 630, a membrane in nozzle 630 is subjected to a periodic disturbance (a vibration), which results in a periodic disruption of the flow of the stream. This periodic disruption of the stream causes the stream to form drops 695. Drops 695 fall into gelling vessel 640, which includes at least one gelling agent. In gelling vessel 640, drops 695 are stabilized by gel formation. During gel formation, the gelling precursor in drops 695 is converted from a solution to a gel form by a gelling agent contained in gelling vessel 640. The gel-stabilized drops are then transferred from gelling vessel 640 to reactor vessel 650, where the polymer in the gel-stabilized drops is reacted (e.g., with a cross-linking agent), to form particles. Thereafter, the particles can be transferred to gel dissolution chamber 660. In gel dissolution chamber 660, the gelling precursor (which was converted to a gel) in the particles is dissolved. After the particle formation process has been completed, the particles can be filtered in filter 670 to remove debris, and sterilized and packaged as a composition including particles.

Methods of making particles are described, for example, in Lanphere et al., U.S. Patent Application Publication No. US 2004/0096662 A1, published on May 20, 2004, and entitled "Embolization", and in DiCarlo et al., U.S. patent application Ser. No. 11/111,511, filed on Apr. 21, 2005, and entitled "Particles", both of which are incorporated herein by reference.

As described above, gelling vessel 640 includes at least one gelling agent. In some embodiments, gelling vessel 640 can include a solution of at least one gelling agent. In certain embodiments, as the concentration of gelling agent in a solution contained in gelling vessel 640 increases, the impedance of particles that are formed using the gelling agent solution can decrease. In some embodiments, the solution in gelling vessel 640 can have a concentration of a gelling agent that is more than about two percent (e.g., more than about five percent, more than about 10 percent, more than about 11 percent, more than about 12 percent, more than about 13 percent, more than about 14 percent, more than about 15 percent, more than about 20 percent, more than about 25 percent, more than about 30 percent, more than about 35 percent, more than about 40 percent, more than about 45 percent, more than about 50 percent, more than about 60 percent, more than about 70 percent, more than about 80 percent, more than about 90 percent), and/or less than about 100 percent (e.g., less than about 90 percent, less than about 80 percent, less than about 70 percent, less than about 60 percent, less than about 50 percent, less than about 45 percent, less than about 40 percent, less than about 35 percent, less than about 30 percent, less than about 25 percent, less than about 20 percent, less than about 15 percent, less than about 14 percent, less than about 13 percent, less than about 12 percent, less than about 11 percent, less than about 10 percent, less than about five percent).

Examples of gelling agents include agents including ions, such as multivalent cations (e.g., divalent cations). Examples of such agents include alkali metal salts, alkaline earth metal salts or transition metal salts that can ionically cross-link with a gelling precursor. In some embodiments, an inorganic salt, such as a calcium, barium, zinc or magnesium salt, can be used as a gelling agent. In certain embodiments (e.g., embodiments in which a gelling precursor is alginate), a suitable gelling agent is calcium chloride. The calcium cations have an affinity for carboxylic groups in the gelling precursor. The cations can complex with carboxylic groups in the gelling precursor, forming a gel. Without wishing to be bound by theory, it is believed that in some embodiments, ions in the gelling agent(s) can help to establish charge balance in a particle that is produced using the gelling agent. It is believed that this charge balance may lead to enhanced ablation. As an example, polyvinyl alcohol typically is negatively charged. If calcium chloride is used as a gelling agent to form a particle including polyvinyl alcohol, calcium cations from the calcium chloride can help to establish charge balance in the particle.

In some embodiments, a particle can be formed by using a solution of one or more gelling precursors in the above-described drop generation process. In some such embodiments, a drop containing the gelling precursor(s) can gel when it contacts the gelling agent, forming a particle including a gel. In certain embodiments, the particle may not be added into reactor vessel 650 and/or gel dissolution chamber 660.

While the use of particles such as particles 10 in an ablation procedure has been described, in some embodiments, particles can be used in other types of procedures.

Figure 10A:
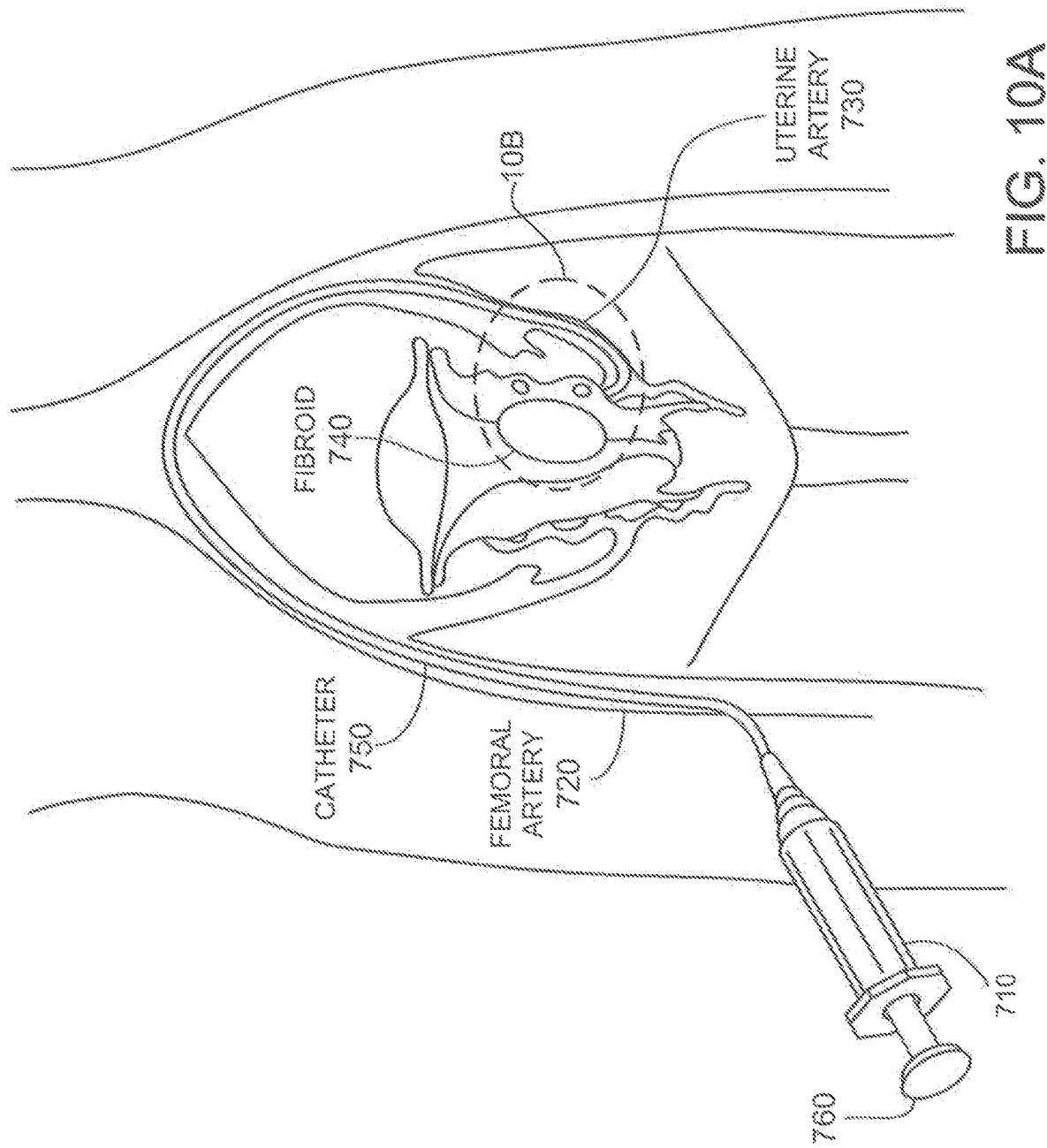
FIG. 10A is a schematic illustrating injection of a composition including particles into a vessel.
Figure 10B:
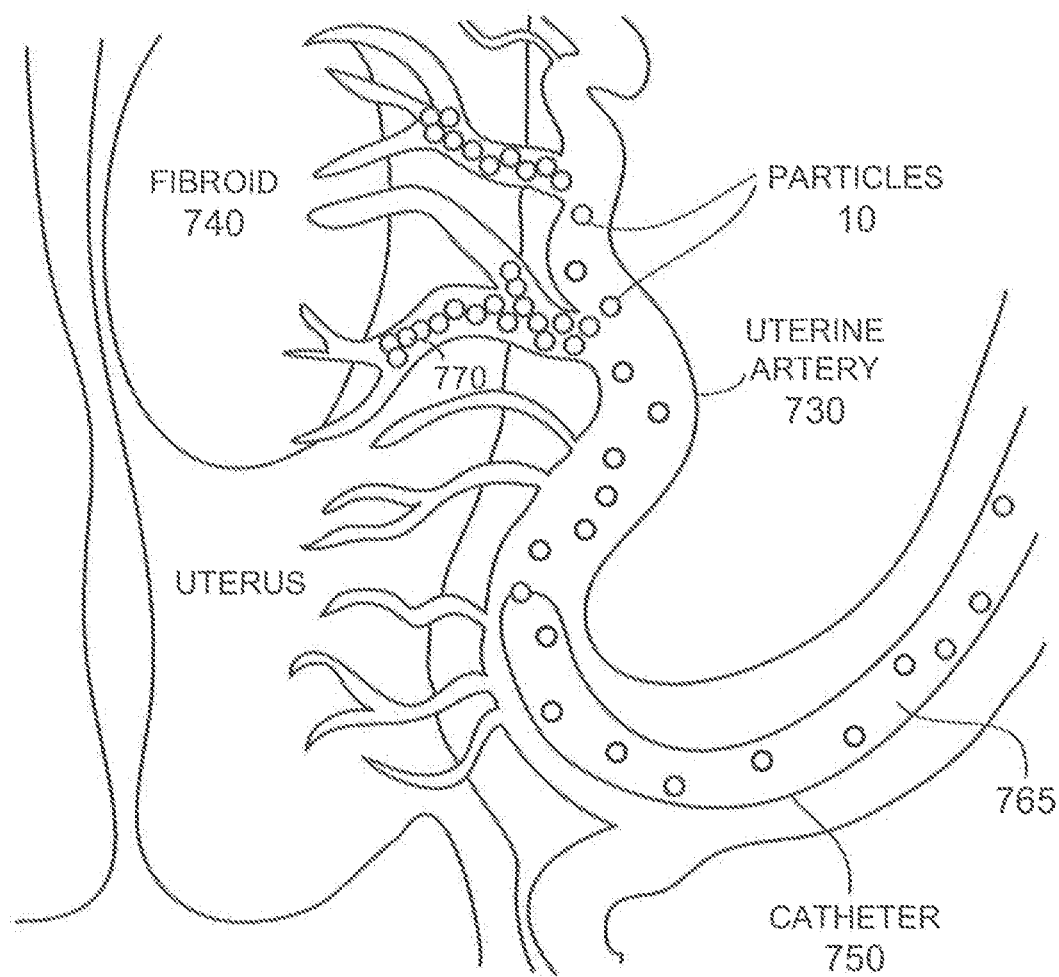
FIG. 10B is an enlarged view of region 10B in FIG. 10A.

For example, FIGS. 10A and 10B show the use of particles 10 in an embolization procedure, in which an embolic composition including particles 10 and a carrier fluid is injected into a vessel through an instrument such as a catheter 750. Catheter 750 is connected to a syringe barrel 710 with a plunger 760. The embolic composition is loaded into syringe barrel 710, and catheter 750 is inserted, for example, into a femoral artery 720 of a patient. Plunger 760 of syringe barrel 710 is then compressed to deliver the embolic composition through catheter 750 into a lumen 765 of a uterine artery 730 that leads to a fibroid 740 located in the uterus of the patient. The embolic composition can, for example, occlude uterine artery 730.

As shown in FIG. 10B, uterine artery 730 is subdivided into smaller uterine vessels 770 (e.g., having a diameter of about two millimeters or less) which feed fibroid 740. Particles 10 in the embolic composition can partially or totally fill the lumen of uterine artery 730, either partially or completely occluding the lumen of uterine artery 730 that feeds uterine fibroid 740.

An embolic composition may be formed of, for example, multiple particles that are combined with a carrier fluid (e.g., a pharmaceutically acceptable carrier, such as a saline solution, a contrast agent, or both). In some embodiments, a composition including particles (e.g., an embolic composition) can include multiple particles that are combined with a calcium chloride solution and/or with water for injection. In general, the density of the particles (e.g., as measured in grams of material per unit volume) can be such that the particles can be readily suspended in the carrier fluid and remain suspended during delivery. In some embodiments, the density of a particle can be from about 1.1 grams per cubic centimeter to about 1.4 grams per cubic centimeter. As an example, for suspension in a saline-contrast solution, the density of a particle can be from about 1.2 grams per cubic centimeter to about 1.3 grams per cubic centimeter.

Compositions including particles (e.g., embolic compositions) can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are, for example, abnormal collections of blood vessels (e.g. in the brain), which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of a composition including particles can vary based on the nature, location and severity of the condition to be treated, as well as the route of administration. A physician treating the condition, disease or disorder can determine an effective amount of the composition. An effective amount of a composition including particles refers to the amount sufficient to result in amelioration of symptoms or a prolongation of survival of the subject, or the amount sufficient to prophylactically treat a subject. The composition can be administered as a pharmaceutically acceptable composition to a subject in any therapeutically acceptable dosage, including those administered to a subject intravenously, intra-arterially, subcutaneously, percutaneously, intratrachealy, intramuscularly, intramucosaly, intracutaneously, intra-articularly, orally or parenterally.

A composition can include a mixture of particles (e.g., particles that include different types of therapeutic agents, particles that have different impedances), or can include particles that are all of the same type. For example, in certain embodiments, particles with a relatively low impedance can be used in conjunction with particles with a relatively high impedance. In some embodiments, a composition can be prepared with a calibrated concentration of particles for ease of delivery by a physician. A physician can select a composition of a particular concentration based on, for example, the type of procedure to be performed. In certain embodiments, a physician can use a composition with a relatively high concentration of particles during one part of a procedure, and a composition with a relatively low concentration of particles during another part of the procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, among the particles delivered to a subject in a composition (e.g., an embolic composition), the majority (e.g., about 50 percent or more, about 60 percent or more, about 70 percent or more, about 80 percent or more, about 90 percent or more) of the particles can have a maximum dimension (e.g., a diameter) of at most about 3,000 microns (e.g., at most about 2,500 microns; at most about 2,000 microns; at most about 1,500 microns; at most about 1,200 microns; at most about 900 microns; at most about 700 microns; at most about 500 microns; at most about 400 microns; at most about 300 microns; at most about 100 microns; at most about 10 microns; at most about five microns) and/or at least about two microns (e.g., at least about five microns; at least about 10 microns; at least about 100 microns; at least about 300 microns; at least about 400 microns; at least about 500 microns; at least about 700 microns; at least about 900 microns; at least about 1,200 microns; at least about 1,500 microns; at least about 2,000 microns; at least about 2,500 microns).

In some embodiments, the arithmetic mean diameter of the particles delivered to a subject in a composition can vary depending upon the particular condition to be treated. As an example, in some embodiments in which the particles in a composition are used to treat a liver tumor, the particles delivered to the subject can have an arithmetic mean diameter of at most about 500 microns (e.g., from about 100 microns to about 300 microns; from about 300 microns to about 500 microns). As another example, in some embodiments in which the particles in a composition are used to treat a uterine fibroid, the particles delivered to the subject in a composition can have an arithmetic mean diameter of at most about 1,200 microns (e.g., from about 500 microns to about 700 microns; from about 700 microns to about 900 microns; from about 900 microns to about 1,200 microns).

In certain embodiments, particles can be linked together to form particle chains. For example, the particles can be connected to each other by links that are formed of one or more of the same material(s) as the particles, or of one or more different material(s) from the particles. Particle chains and methods of making particle chains are described, for example, in Buiser et al., U.S. Patent Application Publication No. US 2005/0238870 A1, published on Oct. 27, 2005, and entitled "Embolization", which is incorporated herein by reference.

In some embodiments, a particle chain can have a relatively low impedance. In certain embodiments, a particle chain can have an impedance of at most 60 ohms (e.g., at most about 55 ohms, at most about 50 ohms, at most about 45 ohms, at most about 40 ohms, at most about 35 ohms, at most about 30 ohms, at most about 25 ohms, at most about 20 ohms, at most about 15 ohms, at most about 10 ohms) at an applied power of at least about two Watts (e.g., two Watts, five Watts, 20 Watts). As referred to herein, the impedance of a particle chain is measured as follows. A mixture including sodium chloride solution (formed of sodium chloride dissolved in deionized water) and multiple particle chains of the same type is drained to remove most of the sodium chloride solution, leaving the particle chains densely packed and just covered by the sodium chloride solution. Two milliliters of the particle chain mixture are then added into a small vial. Two copper wires are used to connect the contents of the vial to an RF 3000® Generator (from Boston Scientific Corp.), with one end of each copper wire being submerged in the particle chain mixture and clipped to the side of the vial by an alligator clip, and the other end of each copper wire being attached to the RF generator by an alligator clip. The copper wires are attached to the vial at a fixed distance of 53.4 millimeters from each other. After the copper wires have been attached to the vial and the generator, the generator is started and the power level is selected. In some embodiments, the power that is applied while measuring the impedance of a particle chain or particle chains can be at least about two Watts (e.g., two Watts, five Watts, 20 Watts). The selected power is applied to the particle chains for a period of about five to 10 seconds, at which point the generator displays the impedance value for the particle chains at the selected applied power.

While particles and particle chains having a relatively low impedance have been described, in some embodiments, a gel can have a relatively low impedance. A gel that has a relatively low impedance may or may not include one or more ferromagnetic materials. In certain embodiments, a gel can have an impedance of at most 60 ohms (e.g., at most about 55 ohms, at most about 50 ohms, at most about 45 ohms, at most about 40 ohms, at most about 35 ohms, at most about 30 ohms, at most about 25 ohms, at most about 20 ohms, at most about 15 ohms, at most about 10 ohms) at an applied power of at least about two Watts (e.g., two Watts, five Watts, 20 Watts).

As referred to herein, the impedance of a gel is measured as follows. If the gel is in a solvent, the solvent first is poured off of the gel. Then, more than about two milliliters (e.g., from about 20 milliliters to about 30 milliliters) of the gel are added into a container such as a petri dish or a beaker. Two copper wires are used to connect the gel to an RF 3000® Generator (from Boston Scientific Corp.), with one end of each copper wire being clipped directly to the gel by an alligator clip, and the other end of each copper wire being attached to the RF generator by an alligator clip. The copper wires are attached to the gel at a fixed distance of 53.4 millimeters from each other. After the copper wires have been attached to the gel and the generator, the generator is started and the power level is selected. In some embodiments, the power that is applied while measuring the impedance of a gel can be at least about two Watts (e.g., two Watts, five Watts, 20 Watts). The selected power is applied to the gel for a period of about five to 10 seconds, at which point the generator displays the impedance value for the gel at the selected applied power.

In certain embodiments, a gel that has a relatively low impedance can be formed at or near a target site. The gel may be formed, for example, in and/or on tissue of a subject (e.g., cancerous tissue). The gel can be formed from components (e.g., liquid components) that can be more easily delivered to the target site than the gel itself would be. Once formed, the gel can exhibit good occlusive properties because, for example, the gel can be tailored to fit the size and/or shape of the target site.

Figure 11:
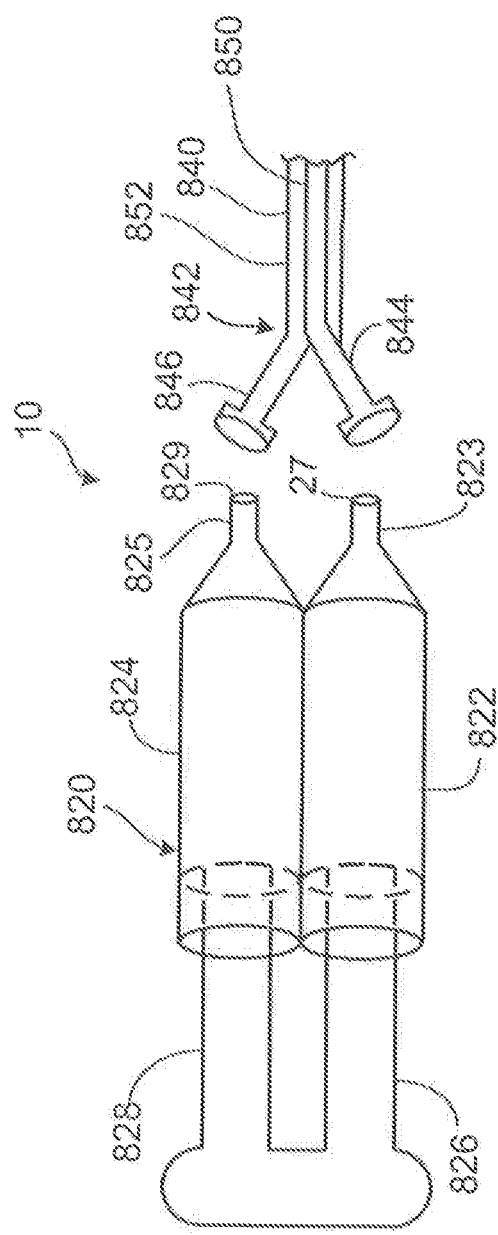
FIG. 11 is a side view of the proximal end portion of an embodiment of a device, as the device is being used in an embolization procedure.
Figure 12:
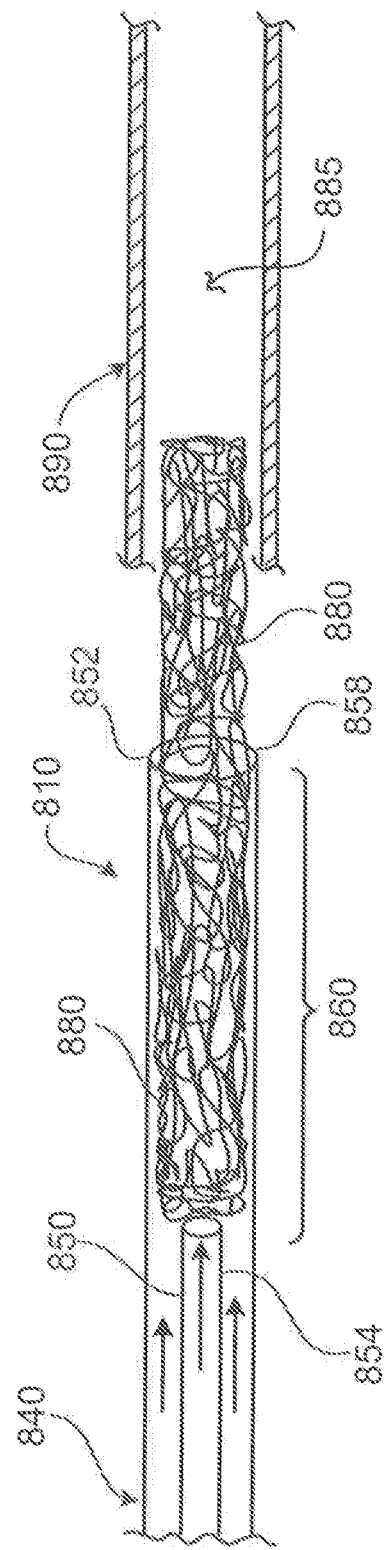
FIG. 12 is a side view of the distal end portion of the device of FIG. 11.

For example, FIGS. 11 and 12 show a delivery device 810 including a double-barrel syringe 820 and a cannula 840 that are capable of being coupled such that substances contained within syringe 820 are introduced into cannula 840. Syringe 820 includes a first barrel 822 having a tip 823 with a discharge opening 827, and a second barrel 824 having a tip 825 with a discharge opening 829. Syringe 820 further includes a first plunger 826 that is movable in first barrel 822, and a second plunger 828 that is movable in second barrel 824. First barrel 822 contains a gelling agent-containing liquid (e.g., calcium chloride in a solvent, such as water or a biocompatible alcohol), while second barrel 824 contains a polymer- and/or gelling precursor-containing liquid (e.g., alginate and a solvent, such as water or a biocompatible alcohol). In its proximal end portion, cannula 840 includes an adapter 842 with a first branch 844 that can connect with tip 823, and a second branch 846 that can connect with tip 825. First branch 844 is integral with a first tubular portion 850 of cannula 840, and second branch 846 is integral with a second tubular portion 852 of cannula 840. First tubular portion 850 is disposed within second tubular portion 852. Delivery devices are described, for example, in Sahatjian et al., U.S. Pat. No. 6,629,947, which is incorporated herein by reference.

When cannula 840 is connected to syringe 820 and plungers 826 and 828 are depressed, the polymer- and/or gelling precursor-containing liquid moves from second barrel 824 into second tubular portion 852, and the gelling agent-containing liquid moves from first barrel 822 into first tubular portion 850. The gelling agent-containing liquid exits first tubular portion 850 and contacts the polymer- and/or gelling precursor-containing liquid in a mixing section 860 of second tubular portion 852. The polymer- and/or gelling precursor-containing liquid and the gelling agent-containing liquid interact to form a gel (e.g., a biocompatible gel) 880 within mixing section 860. Gel 880 exits delivery device 810 at a distal end 858 of mixing section 860, and is delivered into a lumen 885 of a vessel 890 of a subject (e.g., an artery of a human) where gel 880 can embolize lumen 885.

The flow of liquid through first tubular portion 850 and/or second tubular portion 852 can be laminar or non-laminar. One type of non-laminar flow is turbulent flow. In some embodiments, the flow of the gelling agent-containing liquid through first tubular portion 850 and/or the flow of the polymer- and/or gelling precursor-containing liquid through second tubular portion 852 can be helical. In general, helical flow can be laminar or non-laminar (e.g., turbulent). In certain embodiments in which the gelling agent-containing liquid and/or the polymer- and/or gelling precursor-containing liquid exhibit helical flow, the helical flow can help to enhance the degree of mixing between the gelling agent-containing liquid and the polymer- and/or gelling precursor-containing liquid (e.g., in mixing section 860).

Figure 13A:
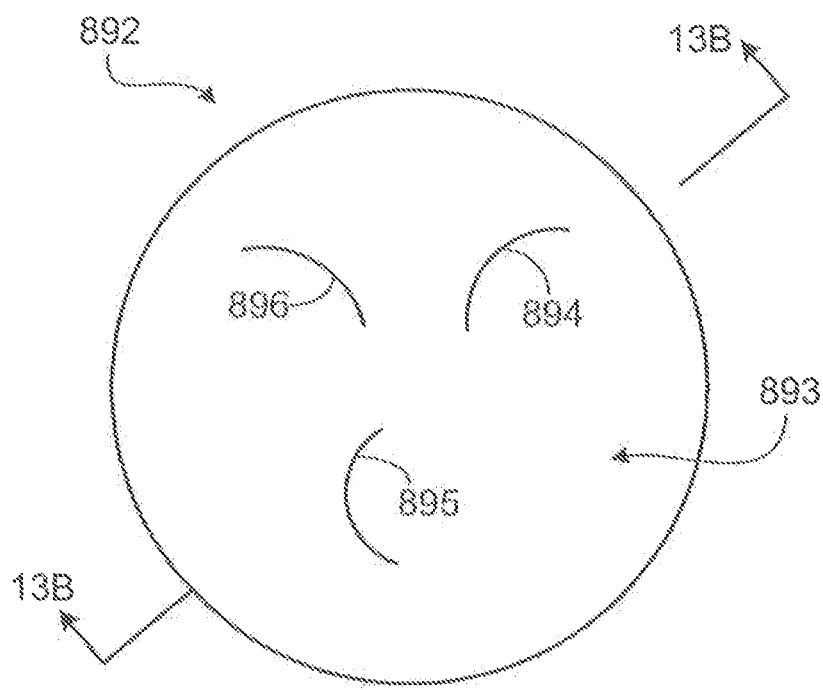
FIG. 13A is a top view of an embodiment of a membrane.
Figure 13B:
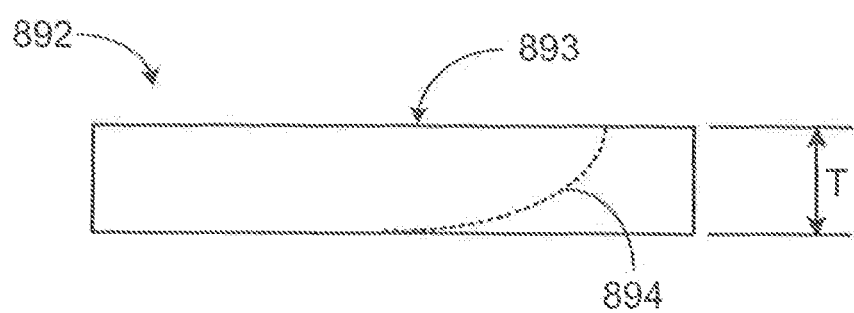
FIG. 13B is a side cross-sectional view of the membrane of FIG. 13A, taken along line 13B-13B.

In some embodiments, a membrane can be used to impart helical flow to a liquid, such as the gelling agent-containing liquid or the polymer- and/or gelling precursor-containing liquid. The membrane may, for example, be located within one or both of first tubular portion 850 and/or second tubular portion 852. FIGS. 13A and 13B show a membrane 892, which has a structure that can impart a helical flow to a liquid that flows through membrane 892. Membrane 892 has a surface plane 893 and three curved slits 15 894, 895, and 896 in surface plane 893. Slits 894, 895, and 896 also have a curvature through the thickness "T" of membrane 892, as shown (for slit 894) in FIG. 13B. In some embodiments, thickness "T" can be at least about 0.01 inch and/or at most about 0.25 inch.

Helical flow, which can be laminar or non-laminar, is described, for example, in DiCarlo et al., U.S. Patent Application Publication No. US 2005/0171510 A1, filed on Aug. 4, 2005, and entitled "Pressure Actuated Safety Valve With Spiral Flow Membrane", and in DiCarlo et al., U.S. patent application Ser. No. 11/111,511, filed on Apr. 21, 2005, and entitled "Particles", both of which are incorporated herein by reference. PCT Application Publication No. WO 02/062271 A1, published on Aug. 15, 2002, and entitled "Valve", discloses, for example, a heart valve with a configuration that allows blood to assume a helical flow path after flowing through the valve, which can reduce or eliminate turbulence and/or dead flow regions in the blood flow. PCT Application Publication No. WO 00/32241, published on Jun. 8, 2000, and entitled "Stents for Blood Vessels", discloses a stent that can be used to support part of a blood vessel and that can be used to cause flow within the vessel to assume a swirling pattern to mimic a flow pattern that can normally be found in arteries. PCT Application Publication No. WO 95/09585, published on Apr. 13, 1995, and entitled "Vascular Prostheses", discloses a vascular prosthesis including a length of generally hollow tubing having at least one curved portion that can induce swirl flow in a liquid when the liquid flows through the curved portion.

While embolization using a gel has been described, in some embodiments, a tissue heating and/or ablation procedure can be conducted using a gel. The gel can, for example, be delivered to and/or formed at a target site (e.g., cancerous tissue), and RF radiation can be applied to the target site to heat and/or ablate the target site.

EXAMPLES

The following examples are intended as illustrative and non-limiting.

Example 1

Preparation of Cross-Linked Polymer Particles
(without Ferromagnetic Material)

Cross-linked polymer particles that did not include ferromagnetic material were prepared according to the following procedure.

An aqueous solution containing 7.06 weight percent polyvinyl alcohol 99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared.

The solution was heated to about 121° C. and filtered through a membrane with openings of less than 100 microns.

The polyvinyl alcohol/sodium alginate solution was then heated to 80° C.

Using a model PHD4400 syringe pump (Harvard Apparatus, Holliston, Mass.), the mixture was fed into a model NISCO Encapsulation unit VAR D drop generator (NISCO Engineering, Zurich, Switzerland).

Drops generated by the drop generator were directed into a gelling vessel containing 20 weight percent calcium chloride in deionized water and stirred with a stirring bar, to form gelled precursor particles or spheres.

The calcium chloride solution was decanted within about three minutes time (for all but the sample 1 gelled precursor particles listed in Table 1 below) to limit leaching of the polyvinyl alcohol from the gelled precursor particles or spheres.

Thereafter, the gelled precursor particles or spheres were processed in different ways for different samples. The sample 1 gelled precursor particles were not rinsed with deionized water, and remained in the 20 weight percent calcium chloride solution, which served as a storage solution. The sample 2 gelled precursor particles were rinsed with deionized water. The sample 3-30 gelled spheres were rinsed with either 200 milliliters of deionized water or 500 milliliters of deionized water, as specified in Table 1. In the processes used to form the sample 3-30 particles, the gelled spheres were added into a reaction vessel containing a solution of four weight percent formaldehyde (37 weight percent in methanol) and 20 weight percent sulfuric acid (95-98 percent concentrated), and the resulting mixture was stirred at 65° C. for 20 minutes.

The resulting precursor particles were rinsed three times with deionized water (300 milliliters of deionized water for each rinsing) to remove residual acidic solution, resulting in particles.

The different types of particles that were prepared are listed in Table 1. The sample 1 and 2 particles were not cross-linked particles, while the sample 3-30 particles all were cross-linked particles. In Table 1, "Sample No." refers to the sample number of the particles that were formed, "Solutions Used" refers to the materials that were used to form the particles, "Result" refers to whether particles were formed (N/A indicates that no particles were formed), "Particle Size (Microns)" refers to the arithmetic mean diameter of the resulting particles in microns (as measured using the Beckman Coulter RapidVUE Image Analyzer version 2.06 (Beckman Coulter, Miami, Fla.)), "Process Specifics" refers to specific details about the process used to make a particular sample of particles, and "Storage Solution" refers to the storage solution that was used to store the particles (N/A indicates that no storage solution was used to store the particles.)

TABLE 1

Cross-Linked Polymer Particles (No Ferromagnetic Material)

| Sample No. | Solutions Used | Result | Particle Size (Microns) | Process Specifics | Storage Solution |
|---|---|---|---|---|---|
| 1 | 7.06 wt % PVA, 1.76 wt % sodium alginate, 20% CaCl₂ | N/A | N/A | Gelled precursor particles were not rinsed with deionized water | 20% CaCl₂ |

TABLE 1-continued

Cross-Linked Polymer Particles (No Ferromagnetic Material)

| Sample No. | Solutions Used | Result | Particle Size (Microns) | Process Specifics | Storage Solution |
|---|---|---|---|---|---|
| 2 | 7.06 wt % PVA, 1.76 wt % sodium alginate, 20% $CaCl_2$ | N/A | N/A | Gelled precursor particles were rinsed with deionized water | N/A |
| 3 | 7.06 wt % PVA, 1.76 wt % sodium alginate, 20% $CaCl_2$ | Cross-linked polymer particles | N/A | Gelled spheres were rinsed twice with 200 milliliters of deionized water; drop generator used a 150-micron nozzle, a 1.400 kHz membrane vibration frequency, and a flow rate of 4.3 milliliters per minute | Unknown |
| 4 | 7.06 wt % PVA, 1.76 wt % sodium alginate, 20% $CaCl_2$ | Cross-linked polymer particles | N/A | Gelled spheres were rinsed once with 200 milliliters of deionized water; drop generator used a 150-micron nozzle, a 1.400 kHz membrane vibration frequency, and a flow rate of 4.3 milliliters per minute | Unknown |
| 5 | 7.06 wt % PVA, 1.76 wt % sodium alginate, 20% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 10% $CaCl_2$ |
| 6 | 7.06 wt % PVA, 1.76 wt % sodium alginate, 20% $CaCl_2$ | Cross-linked polymer | N/A | Gelled spheres were rinsed once with 500 milliliters of deionized water; drop generator used a 150-micron nozzle, a 1.400 kHz membrane vibration frequency, and a flow rate of 4.3 milliliters per minute | 20% $CaCl_2$ |
| 7 | 7.06 wt % PVA, 1.76 wt % sodium alginate, 20% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 30% $CaCl_2$ |
| 8 | 7.06 wt % PVA, 1.76 wt % sodium alginate, 20% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 40% $CaCl_2$ |
| 9 | 7.06 wt % PVA, 1.76 wt % sodium alginate, 10% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 10% $CaCl_2$ |

TABLE 1-continued

Cross-Linked Polymer Particles (No Ferromagnetic Material)

| Sample No. | Solutions Used | Result | Particle Size (Microns) | Process Specifics | Storage Solution |
|---|---|---|---|---|---|
| 10 | 7.06 wt % PVA, 1.76 wt % sodium alginate, 20% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 20% $CaCl_2$ |
| 11 | 7.06 wt % PVA, 1.76 wt % sodium alginate, 30% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 30% $CaCl_2$ |
| 12 | 7.06 wt % PVA, 1.76 wt % sodium alginate, 40% $CaCl_2$ | Cross-linked polymer particles | N/A | Gelled spheres were rinsed once with 500 milliliters of deionized water; drop generator used a 150-micron nozzle, a 1.400 kHz membrane vibration frequency, and a flow rate of 4.3 milliliters per minute | 40% $CaCl_2$ |
| 13 | 7.06 wt % PVA, 1.76 wt % sodium alginate, 20% $CaCl_2$ | Cross-linked polymer particles | 636 microns | Gelled spheres were rinsed once with 500 milliliters of deionized water; drop generator used a 200-micron nozzle, a 850 Hz membrane vibration frequency, and a flow rate of 5.2 milliliters per minute | 20% $CaCl_2$ |
| 14 | 7.06 wt % PVA, 1.76 wt % sodium alginate, 20% $CaCl_2$ | Cross-linked polymer particles | 723 microns | Gelled spheres were rinsed once with 500 milliliters of deionized water; drop generator used a 300-micron nozzle, a 850 Hz membrane vibration frequency, and a flow rate of 10 milliliters per minute | 20% $CaCl_2$ |
| 15 | 7.06 wt % PVA, 1.76 wt % sodium alginate, 2% $CaCl_2$ | Cross-linked polymer particles | 691 microns | Gelled spheres were rinsed once with 500 milliliters of deionized water; drop generator used a 200-micron nozzle, a 850 Hz membrane vibration frequency, and a flow rate of 5.2 milliliters per minute | 2% $CaCl_2$ |
| 16 | 7.06 wt % PVA, 1.76 wt % sodium alginate, 2% $CaCl_2$ | Cross-linked polymer particles | 782 microns | Gelled spheres were rinsed once with 500 milliliters of deionized water; drop generator used a 300-micron nozzle, a 850 Hz membrane vibration frequency, and a flow rate of 10 milliliters per minute | 2% $CaCl_2$ |
| 17 | 7.06 wt % PVA, 1.76 wt % sodium alginate, 2% $CaCl_2$ | Cross-linked polymer particles | 746 microns | Gelled spheres were rinsed once with 500 milliliters of deionized water; drop generator | 20% $CaCl_2$ |

TABLE 1-continued

Cross-Linked Polymer Particles (No Ferromagnetic Material)

| Sample No. | Solutions Used | Result | Particle Size (Microns) | Process Specifics | Storage Solution |
|---|---|---|---|---|---|
| | | | | used a 300-micron nozzle, a 850 Hz vibration frequency, and a flow rate of 10 milliliters per minute | |
| 18 | 7.06 wt % PVA, 1.76 wt % sodium alginate, 20% CaCl$_2$ | Cross-linked polymer particles | 634 microns | Gelled spheres were rinsed once with 500 milliliters of deionized water; drop generator used a 200-micron nozzle, a 850 Hz membrane vibration frequency, and a flow rate of 5.2 milliliters per minute | 0.9% NaCl |
| 19 | 7.06 wt % PVA, 1.76 wt % sodium alginate, 20% CaCl$_2$ | Cross-linked polymer particles | 628 microns | Gelled spheres were rinsed once with 500 milliliters of deionized water; drop generator used a 200-micron nozzle, a 850 Hz membrane vibration frequency, and a flow rate of 5.2 milliliters per minute | 20% CaCl$_2$ |
| 20 | 7.06 wt % PVA, 1.76 wt % sodium alginate, 20% | Cross-linked polymer | 594 microns | Gelled spheres were rinsed once with 500 milliliters of deionized water; drop generator used a 200-micron nozzle, a 850 Hz membrane vibration frequency, and a flow rate of 5.2 milliliters per minute | 0.9% NaCl |
| 21 | 7.06 wt % PVA, 1.76 wt % sodium alginate, 20% CaCl$_2$ | Cross-linked polymer particles | 618 microns | Gelled spheres were rinsed once with 500 milliliters of deionized water; drop generator used a 200-micron nozzle, a 850 Hz membrane vibration frequency, and a flow rate of 5.2 milliliters per minute | 10% NaCl |
| 22 | 7.06 wt % PVA, 1.76 wt % sodium alginate, 20% CaCl$_2$ | Cross-linked polymer particles | 685 microns | Gelled spheres were rinsed once with 500 milliliters of deionized water; drop generator used a 200-micron nozzle, a 850 Hz membrane vibration frequency, and a flow rate of 5.2 milliliters per minute | 5% NaCl |
| 23 | 7.06 wt % PVA, 1.76 wt % sodium alginate, 20% CaCl$_2$ | Cross-linked polymer particles | 684 microns | Gelled spheres were rinsed once with 500 milliliters of deionized water; drop generator used a 200-micron nozzle, a 850 Hz membrane vibration frequency, and a flow rate of 5.2 milliliters per minute | 0.9% NaCl |

TABLE 1-continued

Cross-Linked Polymer Particles (No Ferromagnetic Material)

| Sample No. | Solutions Used | Result | Particle Size (Microns) | Process Specifics | Storage Solution |
|---|---|---|---|---|---|
| 24 | 7.06 wt % PVA, 1.76 wt % sodium alginate, 20% CaCl$_2$ | Cross-linked polymer particles | 684 microns | Gelled spheres were rinsed once with 500 milliliters of deionized water; drop generator used a 200-micron nozzle, a 850 Hz membrane vibration frequency, and a flow rate of 5.2 milliliters per minute | 5% NaCl |
| 25 | 7.06 wt % PVA, 1.76 wt % sodium alginate, 20% CaCl$_2$ | Cross-linked polymer particles | 684 microns | Gelled spheres were rinsed once with 500 milliliters of deionized water; drop generator used a 200-micron nozzle, a 850 Hz membrane vibration frequency, and a flow rate of 5.2 milliliters per minute | 10% NaCl |
| 26 | 7.06 wt % PVA, 1.76 wt % sodium alginate, 20% CaCl$_2$ | Cross-linked polymer particles | 664 microns | Gelled spheres were rinsed once with 500 milliliters of deionized water; drop generator used a 200-micron nozzle, a 850 Hz membrane vibration frequency, and a flow rate of 5.2 milliliters per minute | 5% NaCl |
| 27 | 7.06 wt % PVA, 1.76 wt % sodium alginate, 20% CaCl$_2$ | Cross-linked polymer particles | 660 microns | Gelled spheres were rinsed once with 500 milliliters of deionized water; drop generator used a 200-micron nozzle, a 850 Hz membrane vibration frequency, and a flow rate of 5.2 milliliters per minute | 10% NaCl |
| 28 | 7.06 wt % PVA, 1.76 wt % sodium alginate, 20% CaCl$_2$ | Cross-linked polymer particles | 631 microns | Gelled spheres were rinsed once with 500 milliliters of deionized water; drop generator used a 200-micron nozzle, a 850 Hz membrane vibration frequency, and a flow rate of 5.2 milliliters per minute | 5% NaCl |
| 29 | 7.06 wt % PVA, 1.76 wt % sodium alginate, 20% CaCl$_2$ | Cross-linked polymer particles | 630 microns | Gelled spheres were rinsed once with 500 milliliters of deionized water; drop generator used a 200-micron nozzle, a 850 Hz membrane vibration frequency, and a flow rate of 5.2 milliliters per minute | 10% NaCl |
| 30 | 7.06 wt % PVA, 1.76 wt % sodium alginate, 20% CaCl$_2$ | Cross-linked polymer particles | 701 microns | Gelled spheres were rinsed once with 500 milliliters of deionized water; drop generator used a 200-micron nozzle, a 850 Hz membrane vibration frequency, and a flow rate of 5.2 milliliters per minute | 5% NaCl |

Example 2

Preparation of Cross-Linked Polymer Particles (with Iron Oxide Particles as Ferromagnetic Material)

An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared.

The solution was heated to about 121° C. and filtered through a membrane with openings of less than 100 microns.

Iron oxide particles having a diameter of 200 nanometers (Micromod®, from Micromod Partikeltechnologie GmbH, Friedrich-Barnewitz-Str.4 18119 Rostock-Warnemuende, Germany) were mixed into the polyvinyl alcohol/sodium alginate solution in a 10 weight percent mixture. The mixture was stirred under high shear forces in a conical tube, using a mini-vortexer. The mini-vortexer was a VWR model VM-3000 mini-vortexer, which had a variable speed of from 100 revolutions per minute to 3200 revolutions per minute. The mixture was stirred in the mini-vortexer for at least one minute and at most three minutes, filtered through a membrane with openings of less than 100 microns, and then placed under ultrasonic frequency (to remove air bubbles from the mixture). The filtered mixture was placed under ultrasonic frequency by placing the conical tube containing the mixture under water in an ultrasonic bath (from Branson Ultrasonics Corp.). The ultrasonic bath frequency was 40 Hz.

The polyvinyl alcohol/sodium alginate/iron oxide solution was then heated to 80° C.

Using a model PHD4400 syringe pump (Harvard Apparatus, Holliston, Mass.), the mixture was fed into a model NISCO Encapsulation unit VAR D drop generator (NISCO Engineering, Zurich, Switzerland).

Drops generated by the drop generator were directed into a gelling vessel containing twenty weight percent calcium chloride in deionized water and stirred with a stirring bar.

The calcium chloride solution was decanted within about three minutes time to avoid substantial leaching of the polyvinyl alcohol from the drops, and 500 milliliters of deionized water were added to the gelling vessel.

The deionized water was then decanted, and the drops were added to a reaction vessel containing a solution of four weight percent formaldehyde (37 weight percent in methanol) and 20 weight percent sulfuric acid (95-98 percent concentrated).

The reaction solution was stirred at 65° C. for 20 minutes.

Precursor particles were rinsed three times with deionized water (300 milliliters of deionized water for each rinsing) to remove residual acidic solution, resulting in particles.

Example 3

Preparation of Cross-Linked Polymer Particles (with Magnetite as Ferromagnetic Material)

An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared.

The solution was heated to about 121° C. and filtered through a membrane with openings of less than 100 microns.

Magnetite (EMG 1111 Ferrofluid, from FerroTec Corporation (Nashua, N.H.)) was mixed into the polyvinyl alcohol/sodium alginate solution in a 10 weight percent mixture. The mixture was stirred overnight using a stirring bar, and was filtered through a membrane with openings of less than 100 microns.

The filtered polyvinyl alcohol/sodium alginate/magnetite solution was then heated to 80° C.

Using a model PHD4400 syringe pump (Harvard Apparatus, Holliston, Mass.), the mixture was fed into a model NISCO Encapsulation unit VAR D drop generator (NISCO Engineering, Zurich, Switzerland).

Drops generated by the drop generator were directed into a gelling vessel containing twenty weight percent calcium chloride in deionized water and stirred with a stirring bar.

The calcium chloride solution was decanted within about three minutes time to avoid substantial leaching of the polyvinyl alcohol from the drops, and 500 milliliters of deionized water were added to the gelling vessel.

The deionized water was then decanted, and the drops were added to a reaction vessel containing a solution of four weight percent formaldehyde (37 weight percent in methanol) and 20 weight percent sulfuric acid (95-98 percent concentrated).

The reaction solution was stirred at 65° C. for 20 minutes.

Precursor particles were rinsed three times with deionized water (300 milliliters of deionized water for each rinsing) to remove residual acidic solution, resulting in particles.

Example 4

Preparation of Gel Particles (without Ferromagnetic Material)

Gel particles that did not include ferromagnetic material were prepared according to the following procedure.

An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared.

The solution was heated to about 121° C. and filtered through a membrane with openings of less than 100 microns.

The polyvinyl alcohol/sodium alginate solution was then heated to 80° C.

Using a model PHD4400 syringe pump (Harvard Apparatus, Holliston, Mass.), the mixture was fed into a model NISCO Encapsulation unit VAR D drop generator (NISCO Engineering, Zurich, Switzerland).

Drops generated by the drop generator were directed into a gelling vessel containing twenty weight percent calcium chloride in deionized water and stirred with a stirring bar.

The calcium chloride solution was decanted within about three minutes time to avoid substantial leaching of the polyvinyl alcohol from the drops.

The different types of gel particles that were prepared are listed in Table 2. In Table 2, "Sample No." refers to the sample number of the gel particles that were formed, "Solutions Used" refers to the materials that were used to form the gel particles, "Result" refers to whether gel particles were formed, "Process Specifics" refers to specific details about the process used to make a particular sample of gel particles, and "Storage Solution" refers to the storage solution that was used to store the gel particles.

TABLE 2

Gel Particles (No Ferromagnetic Material)

| Sample No. | Solutions Used | Result | Process Specifics | Storage Solution |
|---|---|---|---|---|
| 31 | 7.06 wt % PVA, 1.76 wt % sodium alginate, 20% $CaCl_2$ | Gel Particles | Gelled spheres were rinsed once with 500 milliliters of deionized water; drop generator used a 200-micron nozzle, a 850 Hz membrane vibration frequency, and a flow rate of 5.2 milliliters per minute | 5% NaCl |

Example 5

Preparation of Gel Particles (with Iron Oxide Particles as Ferromagnetic Material)

Gel particles that included ferromagnetic material were prepared according to the following procedure.

An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG (from FMC Biopolymer, Princeton, N.J.)) in deionized water was prepared.

The solution was heated to about 121° C. and filtered through a membrane with openings of less than 100 microns.

Iron oxide particles having a diameter of 200 nanometers (Micromod®, from Micromod Partikeltechnologie GmbH, Friedrich-Barnewitz-Str.4 18119 Rostock-Warnemuende Germany)) were mixed into the polyvinyl alcohol/sodium alginate solution in a 10 weight percent mixture. The mixture was stirred under high shear forces in a conical tube, using a mini-vortexer. The mini-vortexer was a VWR model VM-3000 mini-vortexer, which had a variable speed of from 100 revolutions per minute to 3200 revolutions per minute. The mixture was stirred in the mini-vortexer for at least one minute and at most three minutes, filtered through a membrane with openings of less than 100 microns, and then placed under ultrasonic frequency (to remove air bubbles from the mixture). The filtered mixture was placed under ultrasonic frequency by placing the conical tube containing the mixture under water in an ultrasonic bath (from Branson Ultrasonics Corp.). The ultrasonic bath frequency was 40 Hz.

The polyvinyl alcohol/sodium alginate/iron oxide solution was then heated to 80° C.

Using a model PHD4400 syringe pump (Harvard Apparatus, Holliston, Mass.), the mixture was fed into a model NISCO Encapsulation unit VAR D drop generator (NISCO Engineering, Zurich, Switzerland). Drops generated by the drop generator were directed into a gelling vessel containing twenty weight percent calcium chloride in deionized water, which was stirred with a stirring bar. The calcium chloride solution was then decanted, and 0.9 weight percent saline was added to form a composition including gel particles and saline.

The different types of gel particles that were prepared are listed in Table 3. In Table 3, "Sample No." refers to the sample number of the particles that were formed, "Solutions Used" refers to the materials that were used to form the particles, "Result" refers to whether gel particles were formed, "Particle Size" refers to the arithmetic mean diameter of the resulting particles in microns (as measured using the Beckman Coulter RapidVUE Image Analyzer version 2.06 (Beckman Coulter, Miami, Fla.)), "Process Specifics" refers to specific details about the process used to make a particular sample of particles, and "Storage Solution" refers to the storage solution that was used to store the particles.

TABLE 3

Gel Particles (Ferromagnetic Material)

| Sample No. | Solutions Used | Result | Particle Size (Microns) | Process Specifics | Storage Solution |
|---|---|---|---|---|---|
| 32 | 7.06 wt % PVA, 1.76 wt % sodium alginate, 20% $CaCl_2$, 5% Micromod | Gel Particles | N/A | Filtering of particles was difficult; drop generator used a 300-micron nozzle, a 850 Hz membrane vibration frequency, and a flow rate of 9 milliliters per minute | 5% NaCl |
| 33 | 7.06 wt % PVA, 1.76 wt % sodium alginate, 20% $CaCl_2$, 10% Micromod | Gel Particles | N/A | Filtering of particles was difficult; drop generator used a 300-micron nozzle, a 850 Hz membrane vibration frequency, and a flow rate of 9 milliliters per minute | 5% NaCl |
| 34 | 7.06 wt % PVA, 1.76 wt % sodium alginate, 20% $CaCl_2$, 10% Micromod | Gel Particles | N/A | Filtering of particles was difficult; drop generator used a 300-micron nozzle, a 850 Hz membrane vibration frequency, and a flow rate of 9 milliliters per minute | 2% $CaCl_2$ |
| 35 | 7.06 wt % PVA, 1.76 wt % sodium alginate, 20% $CaCl_2$, 0% Micromod | Gel Particles | N/A | Gelled particles were rinsed once with 500 milliliters of deionized water; drop generator used a 200-micron | 5% NaCl |

TABLE 3-continued

Gel Particles (Ferromagnetic Material)

| Sample No. | Solutions Used | Result | Particle Size (Microns) | Process Specifics | Storage Solution |
|---|---|---|---|---|---|
| | | | | nozzle, a 850 Hz membrane vibration frequency, and a flow rate of 5.7 milliliters per minute | |
| 36 | 7.06 wt % PVA, 1.76 wt % sodium alginate, 20% CaCl$_2$, 0% Micromod | Gel Particles | N/A | Gelled particles were rinsed once with 500 milliliters of deionized water; drop generator used a 200-micron nozzle, a 850 Hz membrane vibration frequency, and a flow rate of 5.2 milliliters per minute | 5% NaCl |

Example 6

Preparation of Particle Chains, Individual Particles and Strings of Particles

The sample 37 particle chains and individual particles (Table 4) were prepared as follows. An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared. The solution was heated to about 121° C. and filtered through a membrane with openings of less than 100 microns. The polyvinyl alcohol/sodium alginate solution was then heated to 80° C. Using a model PHD4400 syringe pump (Harvard Apparatus, Holliston, Mass.), the mixture was fed into a model NISCO Encapsulation unit VAR D drop generator (NISCO Engineering, Zurich, Switzerland). Drops generated by the drop generator were directed into a gelling vessel containing two weight percent calcium chloride in deionized water filled to the 150 mL line in a 250 mL beaker. The resulting mixture was stirred with a stirring bar. The calcium chloride solution was decanted within about three minutes time to avoid substantial leaching of the polyvinyl alcohol from the drops.

The sample 38 particle chains and individual particles (Table 4) were prepared using the procedure described above for the sample 37 particle chains, except that the stream of solution from the drop generator was cut by hand every two to three seconds using a spatula, and the calcium chloride solution was filled to the 250 mL line in a 250 mL beaker. The resulting sample 38 particle chains included long curled segments of big spheres on a string.

The sample 39 and sample 41 particle chains (Table 4) were prepared using the procedure described above for the sample 38 particle chains, except that the stream of solution from the drop generator was cut by hand every second using a spatula. The resulting sample 39 particle chains included shorter curled lengths of spheres on a string.

The sample 40 particle chains (Table 4) were prepared using the procedure described above for the sample 39 and sample 41 particle chains, except that after the calcium chloride solution was decanted, the drops were added to a reaction vessel containing a solution of four weight percent formaldehyde (37 weight percent in methanol) and 20 weight percent sulfuric acid (95-98 percent concentrated). The reaction solution was stirred at 65° C. for 20 minutes. Precursor particles were rinsed three times with deionized water (300 milliliters of deionized water for each rinsing) to remove residual acidic solution, resulting in particles on a string.

The sample 42 cross-linked strings (Table 4) were prepared as follows. An aqueous solution containing 7.06 weight percent polyvinyl alcohol (99+percent hydrolyzed, average M, 89,000-120,000 (from Aldrich)) and 1.76 weight percent sodium alginate (PRONOVA UPLVG, from FMC Biopolymer, Princeton, N.J.) in deionized water was prepared. The solution was heated to about 121° C. and filtered through a membrane with openings of less than 100 microns. The polyvinyl alcohol/sodium alginate solution was then heated to 80° C. The mixture was then fed into the syringe barrel of a 60 cc syringe with a 0.9ID polished end nozzle (suitable for use with the NISCO VarV1 droplet generator (NISCO Engineering, Zurich, Switzerland)). The mixture-loaded syringe with the nozzle attached was held in hand, and the nozzle tip was submerged in 20% Calcium Chloride. The mixture was then injected into the calcium chloride by hand, thereby generating strings (without generating any particles). The calcium chloride solution was decanted within about three minutes time to avoid substantial leaching of the polyvinyl alcohol from the drops. The strings were then added to a reaction vessel containing a solution of four weight percent formaldehyde (37 weight percent in methanol) and 20 weight percent sulfuric acid (95-98 percent concentrated). The reaction solution was stirred at 65° C. for 20 minutes. Precursor strings were rinsed three times with deionized water (300 milliliters of deionized water for each rinsing) to remove residual acidic solution, resulting in strings.

The sample 43 cross-linked strings (Table 4) were prepared using the procedure described above for the sample 42 cross-linked strings, except that the injection of the polyvinyl alcohol/sodium alginate solution into the calcium chloride solution was intermittently stopped, and the syringe was temporarily removed from the calcium chloride solution. This temporary removal helped to break strings that had formed off of the end of the nozzle, thereby producing some shorter strings than in the sample 42 procedure. After the syringe had been temporarily removed from the calcium chloride solution, the syringe was re-submerged into the solution to make another string.

The different types of particle chains and strings that were prepared are listed in Table 4. In Table 4, "Sample No." refers to the sample number of the particle chains or strings that were formed, "Solutions Used" refers to the materials that were used to form the particle chains or strings, "Result" refers to whether particle chains or strings (and/or individual particles) were formed, "Process Specifics" refers to specific details about the process used to make a particular sample of particle chains or strings, "Storage Solution" refers to the storage solution that was used to store the particle chains or strings, and "Comments" refers to the types of particles included in the particle chains, and to the types of individual particles that formed.

Example 7

Preparation of Gels (without Ferromagnetic Material)

Gels that did not include ferromagnetic material were prepared according to the following procedure.

Twenty-five milliliters of saline solution (from Baxter Healthcare Corp.) were added into a beaker and stirred with a large stir bar at a fast speed. Sodium alginate powder (from FMC Biopolymer, Princeton, N.J.) was added into the saline solution in portions, to allow each portion to wet into the solution. For each sample, the amount of sodium alginate powder that was added was selected to provide the alginate concentration shown in Table 5. During the preparation of

TABLE 4

Particles Chains or Individual Particles

| Sample No. | Solutions Used | Result | Process Specifics | Storage Solution | Comments |
|---|---|---|---|---|---|
| 37 | 7.06 wt % PVA, 1.76 wt % sodium alginate, 2% $CaCl_2$ | Created particle chains and individual particles | Used NISCO Var D 300-micron nozzle, no membrane vibration frequency, and a flow rate of 20 milliliters per minute | 2% $CaCl_2$ | Gel particles |
| 38 | 7.06 wt % PVA, 1.76 wt % sodium alginate, 2% $CaCl_2$ | Created particle chains and individual particles | Used NISCO Var D 300-micron nozzle, no membrane vibration frequency, and a flow rate of 20 milliliters per minute, cut stream with spatula by hand | 2% $CaCl_2$ | Gel particles |
| 39 | 7.06 wt % PVA, 1.76 wt % sodium alginate, 2% $CaCl_2$ | Created particle chains | Used NISCO Var D 300-micron nozzle, no membrane vibration frequency, and a flow rate of 20 milliliters per minute, cut stream with spatula by hand | 2% $CaCl_2$ | Gel particles |
| 40 | 7.06 wt % PVA, 1.76 wt % sodium alginate, 2% $CaCl_2$ | Created particle chains | Used NISCO Var D 300-micron nozzle, no membrane vibration frequency, and a flow rate of 20 milliliters per minute, cut stream with spatula by hand | 20% $CaCl_2$ | Cross-linked Polymer particles |
| 41 | 7.06 wt % PVA, 1.76 wt % sodium alginate, 2% $CaCl_2$ | Created particle chains | Used NISCO Var D 300-micron nozzle, no membrane vibration frequency, and a flow rate of 20 milliliters per minute, cut stream with spatula by hand | 20% $CaCl_2$ | Gel particles |
| 42 | 7.06 wt % PVA, 1.76 wt % sodium alginate, 2% $CaCl_2$ | Created strings without particles | Used a syringe with a NISCO Var V1 Nozzle attached to it, submerged tip of syringe into $CaCl_2$ solution and pushed by hand | 20% $CaCl_2$ | Cross-linked Polymer particles |
| 43 | 7.06 wt % PVA, 1.76 wt % sodium alginate, 2% $CaCl_2$ | Created strings without particles | Used a syringe with a NISCO Var V1 Nozzle attached to it, kept tip of syringe above $CaCl_2$ solution and pushed by hand | 20% $CaCl_2$ | Cross-linked Polymer particles | the sample 44 gel, after the sodium alginate powder had been dissolved into the saline solution, the resulting solution was added into a five percent calcium chloride solution (from EMD Chemicals Inc. (formerly EM Industries, Inc. and EM Science), Gibbstown, N.J.). The resulting mixture was mixed overnight. If some clumps of sodium alginate had not dissolved, then the solution was heated slightly to reduce the viscosity, thereby allowing for faster stirring.

The different types of gels that were prepared are listed in Table 5. In Table 5, "Sample No." refers to the sample number of the gel that was formed, "Solutions Used" refers to the materials that were used to form the gel, "Result" refers to whether a gel was made, "Process Specifics" refers to specific details about the process used to make a particular gel, and "Storage Solution" refers to the storage solution that was used to store the gel (N/A indicates that no storage solution was used to store the gel.)

solution. For each sample, the amount of sodium alginate powder that was added was selected to provide the alginate concentration shown in Table 5. The solution allowed to mix overnight. If some clumps of sodium alginate did not dissolve, then the solution was heated slightly, thereby reducing the viscosity for faster stirring. Once the sodium alginate had dissolved completely into the saline solution, iron oxide particles having a diameter of 200 nanometers (Micromod®, from Micromod Partikeltechnologie GmbH, Friedrich-Barnewitz-Str.4 18119 RostockWarnemuende, Germany) were added into the mixture in an amount selected to provide the Micromod® concentration shown in Table 5, and the mixture was stirred using a VWR model VM-3000 mini-vortexer, which had a variable speed of from 100 revolutions per minute to 3200 revolutions per minute. The mixture was stirred in the mini-vortexer for at least one minute and at most three minutes.

TABLE 5

Gels (No Ferromagnetic Material)

| Sample No. | Solutions Used | Result | Process Specifics | Storage Solution |
|---|---|---|---|---|
| 44 | 2.5% alginate in 0.9% saline with 5% CaCl$_2$ | Thick polymer solution then gelled in CaCl$_2$ | No deionized water used; powder dissolved in NaCl | 5% CaCl$_2$ |
| 45 | 4% alginate dissolved in 0.9% saline | Thick polymer solution (alginate powder dissolved in saline) | No deionized water used; powder dissolved in NaCl | N/A |
| 46 | 4% alginate dissolved in 10% saline | Thick polymer solution (alginate powder dissolved in saline) | No deionized water used; powder dissolved in NaCl | N/A |
| 47 | 4% alginate dissolved in 20% saline | Thick polymer solution (alginate powder dissolved in saline) | No deionized water used; powder dissolved in NaCl | N/A |
| 48 | 6% alginate dissolved in 0.9% saline | Thick polymer solution (alginate powder dissolved in saline) | No deionized water used; powder dissolved in NaCl | N/A |
| 49 | 6% alginate dissolved in 10% saline | Thick polymer solution (alginate powder dissolved in saline) | No deionized water used; powder dissolved in NaCl | N/A |
| 50 | 6% alginate dissolved in 20% saline | Thick polymer solution (alginate powder dissolved in saline) | No deionized water used; powder dissolved in NaCl | N/A |
| 51 | 8% alginate dissolved in 0.9% saline | Thick polymer solution (alginate powder dissolved in saline) | No deionized water used; powder dissolved in NaCl | N/A |
| 52 | 8% alginate dissolved in 20% saline | Thick polymer solution (alginate powder dissolved in saline) | No deionized water used; powder dissolved in NaCl | N/A |
| 53 | 8% alginate dissolved in 20% saline | Thick polymer solution (alginate powder dissolved in saline) | No deionized water used; powder dissolved in NaCl | N/A |

Example 8

Preparation of Gels (with Ferromagnetic Material)

Gels that included ferromagnetic material were prepared according to the following procedure.

Twenty-five milliliters of saline solution (from Baxter Healthcare Corp.) were added into a beaker and stirred with a large stir bar at a fast speed. Sodium alginate powder (from FMC Biopolymer, Princeton, N.J.) was added into the saline solution in portions, to allow each portion to wet into the The different types of gels that were prepared are listed in Table 6. In Table 6, "Sample No." refers to the sample number of the gel that was formed, "Solutions Used" refers to the materials that were used to form the gel, "Result" refers to whether a gel was made, "Process Specifics" refers to specific details about the process used to make a particular gel, and "Storage Solution" refers to the storage solution that was used to store the gel (N/A indicates that no storage solution was used to store the gel.)

TABLE 6

Gels (With Ferromagnetic Material)

| Sample No. | Solutions Used | Result | Process Specifics | Storage Solution |
|---|---|---|---|---|
| 54 | 9% alginate and 10% Micromod in 0.9% saline | Thick polymer solution (alginate powder dissolved in saline) | No deionized water used; powder dissolved in NaCl | N/A |
| 55 | 10% alginate and 10% Micromod in 0.9% saline | Thick polymer solution (alginate powder dissolved in saline) | No deionized water used; powder dissolved in NaCl | N/A |

While certain embodiments have been described, other embodiments are possible.

Figure 14:
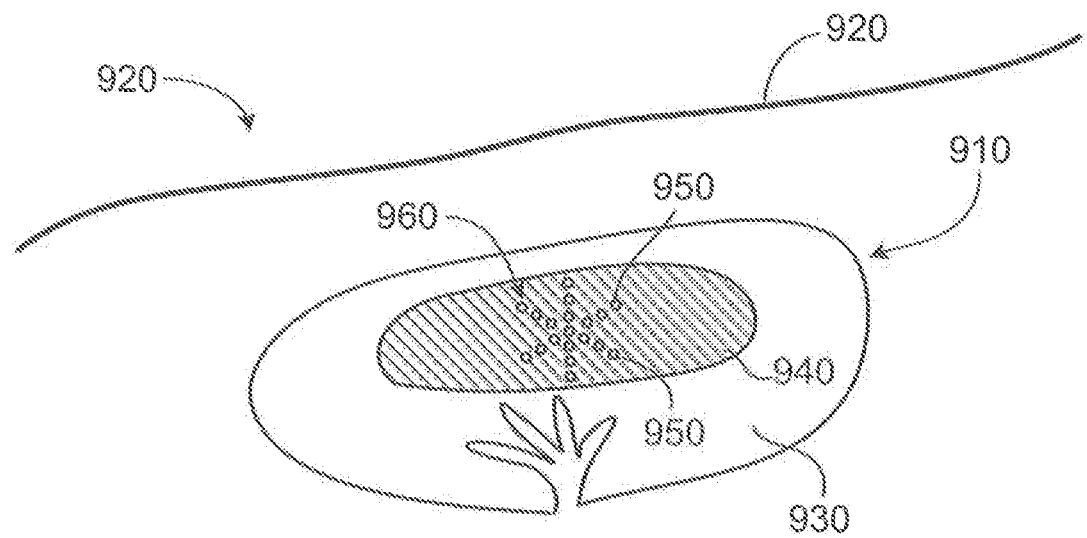
FIG. 14 is a cross-sectional view of a cancerous liver of a subject.

As an example, while the formation of a circle of particles at a target site has been described, in some embodiments, a different pattern of particles can be formed at a target site. For example, FIG. 14 shows a portion 900 of a subject including a liver 910 and skin 920. Liver 910 includes healthy tissue 930 and unhealthy tissue 940. Particles 950 are arranged in unhealthy tissue 940 in a starburst pattern 960. Other patterns of particles that can be formed at a target site include, for example, squares, rectangles, ovals, and triangles.

Figure 15:
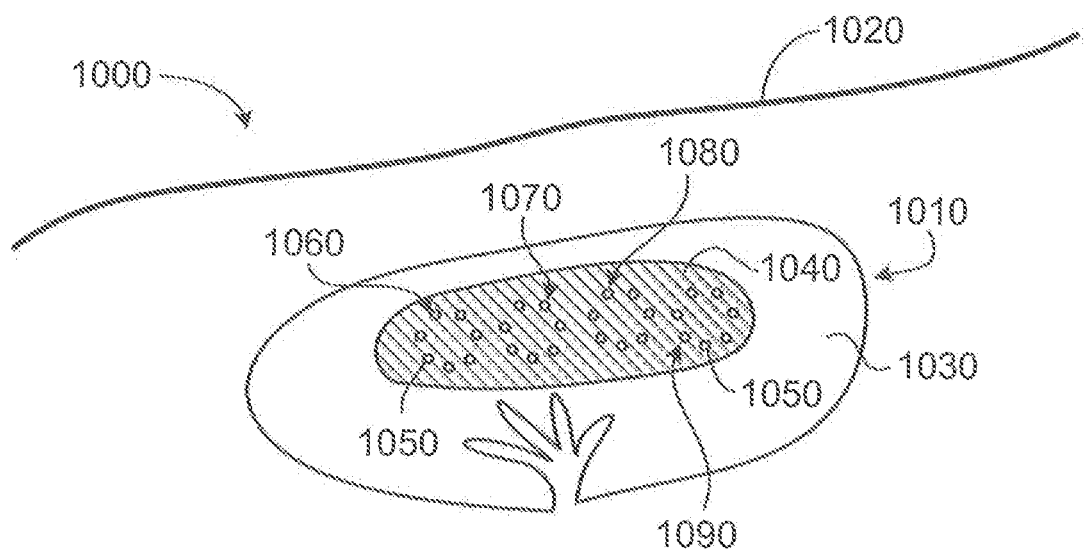
FIG. 15 is a cross-sectional view of a cancerous liver of a subject.

As another example, in some embodiments, multiple (e.g., two, three, four, five, 10) patterns of particles can be formed at a target site. The patterns that are formed at a target site can be the same as each other or different from each other. For example, FIG. 15 shows a portion 1000 of a subject including a liver 1010 and skin 1020. Liver 1010 includes healthy tissue 1030 and unhealthy tissue 1040. Particles 1050 are arranged in unhealthy tissue 1040 in the form of four circles 1060, 1070, 1080, and 1090.

As an additional example, in some embodiments, particles, particle chains, and/or gels can be used in an ablation procedure in conjunction with one or more other materials that can be used to enhance tissue heating and/or ablation. Examples of materials that can be used to enhance tissue heating and/or ablation include saline, acetic acid, ethanol gels, and ferromagnetic material (e.g., ferromagnetic particles). For example, particles and saline can be simultaneously delivered to a target site (e.g., cancerous tissue), or particles can be delivered to a target site, followed by saline.

As a further example, while ablation systems using RF energy have been described, in some embodiments, a microwave ablation system can be used in an ablation and/or heating procedure. Examples of microwave ablation systems include the VivaWave™ Microwave Ablation System (from Vivant Medical, Inc., Mountain View, Calif.), and the Microsulis Tissue Ablation (MTA) system (from Microsulis Medical Limited, Hampshire, England). In some embodiments in which a microwave ablation system is used in conjunction with particles, particle chains, and/or gels in an ablation and/or heating procedure, the maximum distance between an antenna of the microwave ablation system and a particle, particle chain, and/or gel can be at most about 10 centimeters (e.g., at most about eight centimeters, at most about five centimeters, at most about two centimeters). Microwave ablation systems are described, for example, in Cronin, U.S. Pat. No. 6,635,055.

As an additional example, while RF electrodes having tines have been described, in some embodiments, an electrode used in an ablation procedure may not have tines. For example, an electrode (e.g., an RF electrode) can include a single needle or rod. In some embodiments, an antenna can be used in an ablation procedure (e.g., a microwave ablation procedure).

As a further example, while ablation procedures using electrodes have been described, in some embodiments, an ablation procedure may not use an electrode, or may use an electrode in conjunction with another source of energy. For example, in certain embodiments (e.g., in certain embodiments in which particles include one or more ferromagnetic materials), a magnetic field can be applied to particles to adjust the conductivity of the particles. The magnetic field can be applied, for example, using a magnetic resonance imaging (MRI) system. In some embodiments, a change in the conductivity of the particles can result in a change in the extent of heating and/or ablation effected by the particles. The application of a magnetic field to particles is described, for example, in Rioux et al., U.S. Patent Application Publication No. US 2004/0101564 A1, published on May 27, 2004, and entitled "Embolization", which is incorporated herein by reference.

As another example, in some embodiments, a particle can be formed of one or more materials with a relatively high impedance (e.g., at least about 250 ohms), but can include a coating that is formed of one or more materials with a relatively low impedance (e.g., at most about 20 ohms).

As an additional example, while the heating and/or ablation of tissue using RF radiation has been described, in certain embodiments, microwave radiation can be used to heat and/or ablate tissue.

As a further example, while certain embodiments of RF electrodes have been described, other embodiments of RF electrodes may be used in a tissue heating and/or ablation procedure. For example, while array electrodes have been described, in some embodiments, a non-array electrode (e.g., a needle or a rod) can be used in a tissue heating and/or ablation procedure. In certain embodiments, a non-array electrode can be used to heat and/or ablate a relatively small area of tissue (e.g., breast tissue, lung tissue), such as an area having a maximum dimension of from about one centimeter to about two centimeters. In some embodiments, an array electrode can be used to heat and/or ablate a relatively large area of tissue (e.g., liver tissue, lung tissue), such as an area having a maximum dimension of more than two centimeters. Examples of RF electrodes include monopolar RF electrodes and bipolar RF electrodes, such as LeVeen monopolar needle electrodes (Boston Scientific Corp.), and the Concerto™ Bipolar Needle Electrode (Boston Scientific Corp.).

As another example, in some embodiments, a particle, a particle chain, and/or a gel can include one or more therapeutic agents (e.g., drugs). In certain embodiments, a particle, a particle chain, and/or a gel can include a coating that includes one or more therapeutic agents (e.g., thrombogenic agents). In some embodiments, a particle, a particle chain, and/or a gel can have a coating that includes a high concentration of one or more therapeutic agents. One or more of the therapeutic agents can also be loaded into the interior region of a particle and/or a gel. Thus, the surface of the particle and/or gel can release an initial dosage of therapeutic agent after which the body of the particle and/or gel can provide a burst release of therapeutic agent. The therapeutic agent on the surface of the particle and/or gel can be the same as or different from the therapeutic agent in the body of the particle and/or gel. The therapeutic agent on the surface can be applied by exposing the particle and/or gel to a high concentration solution of the therapeutic agent. The therapeutic agent coated particle and/or gel can include another coating over the surface the therapeutic agent (e.g., a degradable and/or bioabsorbable polymer which erodes when the particle is administered). The coating can assist in controlling the rate at which therapeutic agent is released from the particle and/or gel. For example, the coating can be in the form of a porous membrane. The coating can delay an initial burst of therapeutic agent release. The coating can be applied by dipping or spraying the particle and/or gel. The coating can include therapeutic agent or can be substantially free of therapeutic agent. The therapeutic agent in the coating can be the same as or different from an agent on a surface layer of the particle and/or gel, and/or within the particle and/or gel. A polymer coating (e.g. an erodible coating) can be applied to the particle surface and/or gel surface in embodiments in which a high concentration of therapeutic agent has not been applied to the particle surface and/or gel surface. Coatings are described, for example, in DiMatteo et al., U.S. Patent Application Publication No. US 2004/0076582 A1, published on Apr. 22, 2004, and entitled "Agent Delivery Particle", which is incorporated herein by reference. In some embodiments, one or more particles, particle chains, and/or gels can be disposed in a therapeutic agent that can serve as a pharmaceutically acceptable carrier.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a noninfectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; antiproliferative agents (e.g., agents capable of blocking smooth muscle cell proliferation, such as rapamycin); calcium entry blockers (e.g., verapamil, diltiazem, nifedipine); and survival genes which protect against cell death (e.g., anti-apoptotic Bcl-2 family factors and Akt kinase).

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor a and 13, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgrl), BMP7 (0P1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

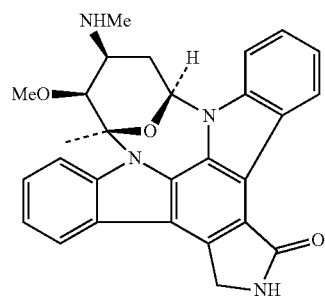

as well as diindoloalkaloids having one of the following general structures:

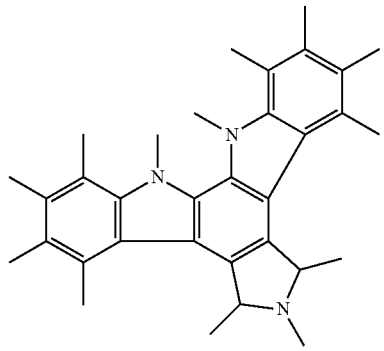

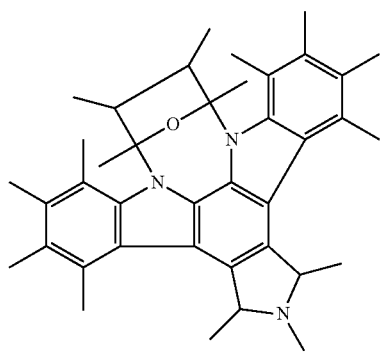

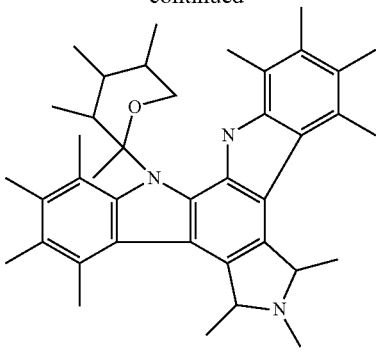

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or 12.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including a-antagonists (e.g., prazosin, bunazosine), 13-antagonists (e.g., propranolol), and a/13-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and 5natural polymers/oligomers), C-nitroso-, 0-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, (3-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-I3 pathway agents such as polyanionic agents (heparin, fucoidin), decorin, and TGF-I3 antibodies, EGF pathway agents (e.g., EGF antibodies, receptor antagonists, chimeric fusion proteins), TNF-a pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in DiMatteo et al., U.S. Patent Application Publication No. US 2004/0076582 A1, published on Apr. 22, 2004, and entitled "Agent Delivery Particle", and in Schwarz et al., U.S. Pat. No. 6,368,658, both of which are incorporated herein by reference.

As an additional example, in some embodiments, a particle can include a shape memory material, which is capable of being configured to remember (e.g., to change to) a predetermined configuration or shape. In certain embodiments, a particle that includes a shape memory material can be selectively transitioned from a first state to a second state. For example, a heating device provided in the interior of a delivery catheter can be used to cause a particle including a shape memory material to transition from a first state to a second state. Shape memory materials and particles that include shape memory materials are described, for example, in Bell et al., U.S. Patent Application Publication No. US 2004/0091543 A1, published on May 13, 2004, and entitled "Embolic Compositions", and in DiCarlo et al., U.S. Patent Application Publication No. US 2005/0095428 A1, published on May 5, 2005, and entitled "Embolic Compositions", both of which are incorporated herein by reference.

As a further example, in certain embodiments, a particle can include a surface preferential material. Surface preferential materials are described, for example, in DiCarlo et al., U.S. Patent Application Publication No. US 2005/0196449 A1, published on Sep. 8, 2005, and entitled "Embolization", which is incorporated herein by reference.

As another example, in some embodiments, a particle can include one or more diagnostic agents (e.g., a radiopaque material, a material that is visible by magnetic resonance imaging (an MRI-visible material), an ultrasound contrast agent). In certain embodiments, a diagnostic agent can be added to a particle by injection of the diagnostic agent into the particle and/or by soaking the particle in the diagnostic agent. Diagnostic agents are described, for example, in Rioux et al., U.S. Patent Application Publication No. US 2004/0101564 A1, published on May 27, 2004, and entitled "Embolization", which is incorporated herein by reference.

As an additional example, in some embodiments, particles having different shapes, sizes, physical properties, and/or chemical properties, can be used together in a procedure (e.g., an ablation procedure, an embolization procedure). For example, particles having different impedances can be used together in an ablation procedure. The different particles can be delivered into the body of a subject in a predetermined sequence or simultaneously. In certain embodiments, mixtures of different particles can be delivered using a multi-lumen catheter and/or syringe. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in Bell et al., U.S. Patent Application Publication No. US 2004/0091543 A1, published on May 13, 2004, and entitled "Embolic Compositions", and in DiCarlo et al., U.S. Patent Application Publication No. US 2005/0095428 A1, published on May 5, 2005, and entitled "Embolic Compositions", both of which are incorporated herein by reference.

As another example, in some embodiments, particles can be lyophilized (e.g., using a VirTis Sentry™ lyophilizer (SP Industries, Gardiner, N.Y.)). In certain embodiments, lyophilized particles can be reconstituted shortly before a procedure (e.g., an ablation procedure).

As a further example, in some embodiments particles can be used for tissue bulking. As an example, particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in Bourne et al., U.S. Patent Application Publication No. US 2003/0233150 A1, published on Dec. 18, 2003, and entitled "Tissue Treatment", which is incorporated herein by reference.

As another example, in some embodiments, a gas (e.g., air, nitrogen, argon, krypton, helium, neon) can be bubbled through a gelling agent mixture (e.g., a gelling agent solution) in a vessel. In certain embodiments, an air pump (e.g., an Accuculture air pump) can be used to pump air into a gelling agent mixture. Without wishing to be bound by theory, it is believed that in some embodiments, bubbling a gas through a gelling agent mixture may reduce the surface tension of the mixture and/or result in the formation of relatively small particles (e.g., particles having a diameter of less than about 500 microns).

As an additional example, while certain drop generators have been described, in some embodiments, other types of drop generators can be used to make particles. Examples of commercially available drop generators include the Inotech Encapsulator unit IE-50R/NS (Inotech AG, Dottikon, Switzerland) and the Genialab® JetCutter Type S (from Genialab). Drop generators are described, for example, in DiCarlo et al., U.S. patent application Ser. No. 11/111,511, filed on Apr. 21, 2005, and entitled "Particles", which is incorporated herein by reference.

Other embodiments are in the claims.

The invention claimed is:

1. A method, comprising:
forming a gel at a target site in a tissue of a subject, wherein the gel has an impedance of at most 60 ohms at an applied power of two Watts, wherein forming the gel comprises disposing a plurality of liquid components in the tissue of the subject to form the gel, and wherein disposing the plurality of liquid components in the tissue of the subject to form the gel includes discharging the plurality of liquid components from a delivery device comprising a double-barrel syringe that contains the plurality of liquid components, a mixing section comprising a membrane having a plurality of curved slits, and a cannula that is coupled to the double-barrel syringe, wherein the plurality of liquid components within the double-barrel syringe are introduced into the cannula through the membrane;

positioning an RF electrode at the target site; and applying RF energy to the target site through the RF electrode to heat the tissue.

2. The method of claim 1, wherein the gel has an impedance of at most about 40 ohms at an applied power of two Watts.

3. The method of claim 1, wherein the gel does not comprise a ferromagnetic material.

4. The method of claim 1, wherein the gel comprises a ferromagnetic material.

5. The method of claim 1, further comprising the step of at least partially occluding a body lumen.

6. The method of claim 1, wherein the plurality of liquid components includes a gelling agent-containing liquid and a gelling precursor-containing liquid.

7. The method of claim 6, wherein the RF electrode has a plurality of tines and is deployed at the target site and where the RF energy flows through the plurality of tines and heats the tissue.

8. The method of claim 6, wherein the gelling precursor-containing liquid comprises an ionically cross-linkable polymer and wherein the gelling agent-containing liquid comprises a multivalent cation.

9. The method of claim 8, wherein the gelling precursor-containing liquid comprises a water soluble polysaccharide.

10. The method of claim 8, wherein the gelling precursor-containing liquid comprises alginate and wherein the gelling agent comprises a multivalent cation.

11. The method of claim 8, wherein the RF electrode has a plurality of tines and is deployed at the target site and where the RF energy flows through the plurality of tines and heats the tissue.

12. The method of claim 1, wherein the RF electrode has a plurality of tines and is deployed at the target site and where the RF energy flows through the plurality of tines and heats the tissue.

13. The method of claim 1, wherein the plurality of liquid components includes a gelling agent-containing liquid and a gelling precursor-containing liquid, and wherein the double-barrel syringe comprises a first barrel that contains the gelling agent-containing liquid and a second barrel that contains the gelling precursor-containing liquid.

14. The method of claim 13, wherein the gelling precursor-containing liquid comprises alginate and wherein the gelling agent-containing liquid comprises a multivalent cation.

15. The method of claim 13, wherein the gelling precursor-containing liquid comprises an ionically cross-linkable polymer and wherein the gelling agent-containing liquid comprises a multivalent cation.

16. The method of claim 15, wherein the gelling precursor-containing liquid comprises a water soluble polysaccharide.

* * * * *